United States Patent
Itou et al.

(10) Patent No.: US 6,511,462 B1
(45) Date of Patent: Jan. 28, 2003

(54) CATHETER AND METHOD OF MANUFACTURING THE SAME

(75) Inventors: Takenari Itou, Fujinomiya (JP); Nobuaki Mihara, Fujinomiya (JP)

(73) Assignee: Terumo Kabushiki Kaisha, Tokyo (JP)

( * ) Notice: Subject to any disclaimer, the term of this patent is extended or adjusted under 35 U.S.C. 154(b) by 245 days.

(21) Appl. No.: 09/614,589

(22) Filed: Jul. 12, 2000

(30) Foreign Application Priority Data

Jul. 16, 1999 (JP) ............................................ 11-202607

(51) Int. Cl.[7] ............................................. A61M 25/00
(52) U.S. Cl. ...................... 604/264; 604/523; 604/524; 604/525; 604/526; 604/527; 264/463
(58) Field of Search .......................... 138/123; 264/405, 264/463, 564, 513; 604/264, 523, 524, 525, 526, 527

(56) References Cited

U.S. PATENT DOCUMENTS

| 5,103,543 A | 4/1992 | Hodgson ..................... 29/173 |
| 5,176,661 A | 1/1993 | Evard et al. ................. 604/282 |
| 5,312,356 A | 5/1994 | Engelson et al. ........... 604/164 |
| 5,454,795 A | 10/1995 | Samson ....................... 604/282 |
| 5,456,674 A | 10/1995 | Bos et al. .................... 604/280 |
| 5,538,513 A | * 7/1996 | Okajima ...................... 138/124 |
| 5,695,483 A | 12/1997 | Samson ....................... 604/282 |
| 5,792,124 A | 8/1998 | Horrigan et al. ............ 604/282 |
| 5,836,926 A | * 11/1998 | Peterson et al. ............ 604/264 |
| 6,030,371 A | * 2/2000 | Pursley ........................ 427/195 |
| 6,165,163 A | * 12/2000 | Chien et al. ................ 604/523 |
| 6,217,565 B1 | * 4/2001 | Cohen ......................... 604/525 |

FOREIGN PATENT DOCUMENTS

WO          98/07523          2/1998

* cited by examiner

*Primary Examiner*—Thomas Denion
*Assistant Examiner*—Ching Chang
(74) *Attorney, Agent, or Firm*—Burns, Doane, Swecker & Mathis, LLP

(57) ABSTRACT

A first linear member made of a first resin material having a relatively high rigidity is wound in a dense spiral in a first region and in a sparse spiral in a second region of a base tube for a catheter, and a second linear member made of a second resin material having a relatively low rigidity is wound in a sparse spiral in the first region and in a dense spiral in the second region of the base tube. Then, the first linear member and the second linear member are melted by heating, followed by solidifying the molten materials, thereby forming a catheter excellent in pushability, torque transmitting capability, following capability, kink resistance and safety.

27 Claims, 9 Drawing Sheets

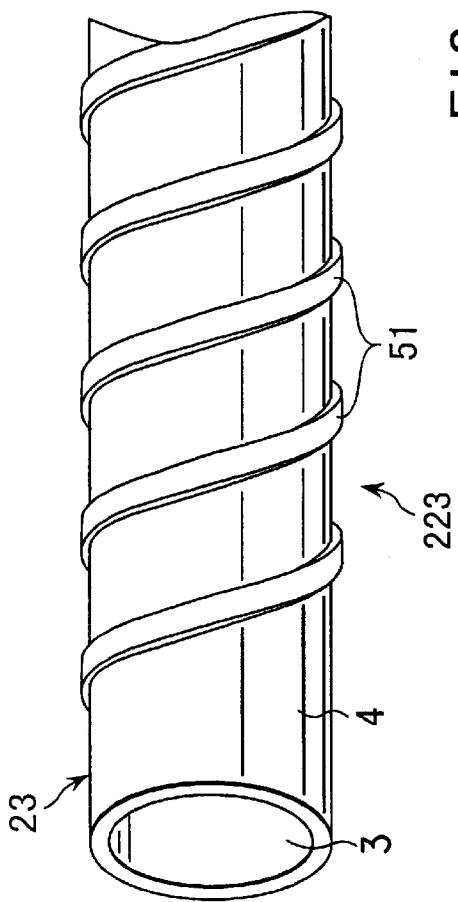
FIG. 4
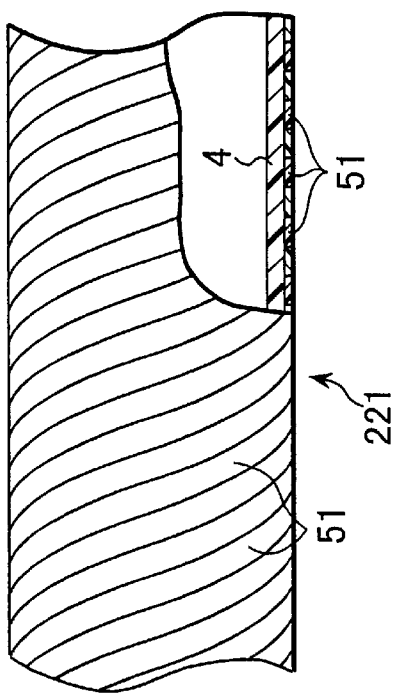
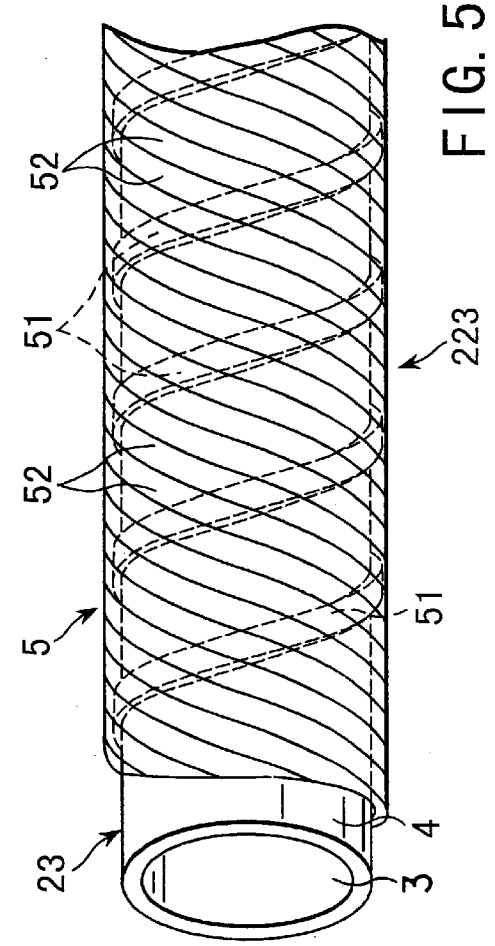
FIG. 5
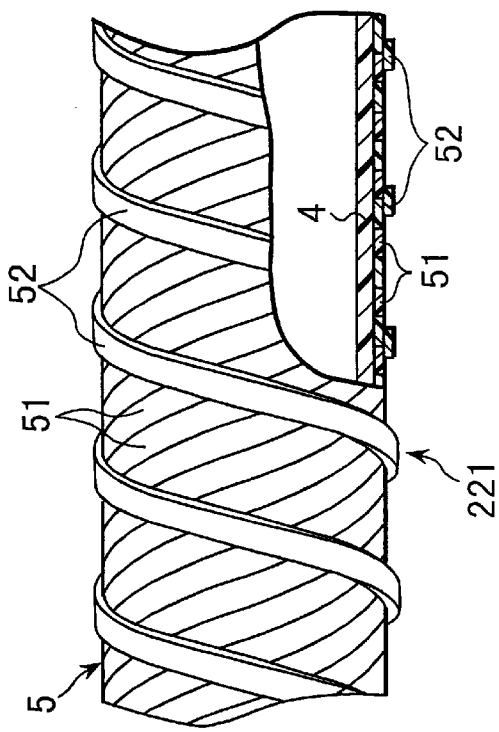

CATHETER AND METHOD OF MANUFACTURING THE SAME

CROSS-REFERENCE TO RELATED APPLICATIONS

This application is based upon and claims the benefit of priority from the prior Japanese Patent Application No. 11-202607, filed Jul. 16, 1999, the entire contents of which are incorporated herein by reference.

BACKGROUND OF THE INVENTION

The present invention relates to a catheter inserted into, for example, a blood vessel for use and a method of manufacturing the catheter.

In general, in performing a selective angiography or angioplasty, used are, for example, an angiography catheter, a guiding catheter, a dilatation catheter and an embolotherapy catheter (microcatheter).

Such a catheter is required to exhibit an excellent operability to permit the catheter to be inserted promptly and with an ensured selectivity into vasculature of a fine complex pattern.

The catheter is also required to have an outer diameter as small as possible while ensuring a predetermined inner diameter in order to widen the range of selection in the insertion region, to alleviate strain given to the patient, and to improve the operability in inserting the catheter into, for example, a blood vessel.

The catheter is required to meet various operability including, for example, pushing capability (pushability) that the pushing force of the operator for moving forward the catheter within a blood vessel can be transmitted from the proximal end of the catheter to the distal end; torque transmitting capability (trackability) that the turning force applied to the proximal end of the catheter can be transmitted to the distal end without fail; the following capability that the catheter is capable of following smoothly and without fail the guide wire preceding the catheter within a curved blood vessel; and kink resistance that, even after the guide wire is withdrawn after the distal end of the catheter has reached a desired region, the catheter is not kinked in the curved portion of the blood vessel. The catheter is also required to exhibit safety that the distal end of the catheter does not damage the inner wall of the blood vessel.

In order to obtain a good pushability and a good torque transmitting capability, it is desirable for the catheter to be formed of a relatively hard material except the distal end portion. In order to obtain a good following capability and safety, it is desirable for the distal end portion of the catheter to be formed of a relatively soft material.

As a catheter meeting the above-noted requirements, a catheter prepared by joining unit tubes made of different materials disclosed in, for example, U.S. Pat. No. 5,792,124, and a catheter prepared by co-extruding a plurality of different kinds of resins, disclosed in, for example, U.S. Pat. No. 5,456,674, are known.

However, the catheter prepared by joining unit tubes made of different materials is likely to be cut away because of decrease in the bonding strength at the joining portion. To overcome this difficulty, it is necessary to increase the thickness of the tube, i.e., the difference between the inner and outer diameters of the tube, making it difficult to diminish the outer diameter of the tube. Also, stepped portions are formed on the outer surface in the joining portions, with the result that the inner wall of the blood vessel tends to be damaged when the catheter is inserted into the blood vessel. In addition, since the rigidity is rapidly changed in the joining portion, the catheter tends to be kinked at the joining portion. In other words, the catheter is not satisfactory in the kink resistance.

On the other hand, a costly manufacturing apparatus is required in the method of manufacturing a catheter by the co-extrusion of a plurality of different kinds of resins, making the method impractical.

BRIEF SUMMARY OF THE INVENTION

An object of the present invention is to provide a catheter excellent in operability such as the pushability, the torque transmitting capability, the following capability and the kink resistance and a method of manufacturing the catheter that is advantageous in making the catheter small in its outer diameter.

According to a first aspect of the present invention, there is provided a method of manufacturing a catheter having a proximal end, a distal end and a tubular member defining an inner lumen extending between the proximal end and the distal end, the method comprising steps of: preparing a first linear member made of a first resin material and a second linear member made of a second resin material; disposing the first linear member in a dense spiral or mesh in a first region of the tubular member and in a sparse spiral or mesh in a second region of the tubular member; and disposing the second linear member in a sparse spiral or mesh in the first region of the tubular member and in a dense spiral or mesh in the second region of the tubular member.

The method of the present invention may further comprise steps of: disposing the first linear member in an intermediate region between the first and second regions in a spiral or mesh of a disposing density intermediate between the disposing densities in the first and second regions; and disposing the second linear member in an intermediate region between the first and second regions in a spiral or mesh of a disposing density intermediate between the disposing densities in the first and second regions.

In this case, the first region, the intermediate region and the second region are arranged in the order mentioned as viewed from the proximal end of the catheter.

To be more specific, the method of the present invention is performed by, for example, rotating the supply source of the first linear member and the supply source of the second linear member around the tubular member and by adjusting the relative rotating speeds of the supply sources of the first and second linear members so as to adjust the disposing densities of the first and second linear members on the tubular member.

In the method of the present invention, it is desirable for the first linear member to have a flexural rigidity higher than that of the second linear member.

The method of the present invention may further comprise steps of: melting at least partially the first and second linear members disposed on the tubular member so as to mix or fuse the first and second linear members; and solidifying the molten portion.

The method of the present invention may further comprise a step of covering the first and second linear members disposed on the tubular member with a heat shrinkable tube and heating the resultant product, thereby melting at least partially the first and second linear members so as to mix or fuse these first and second linear members and solidifying these first and second linear members.

The method of the present invention may further comprise a step of disposing the first linear member alone in a region on the side of the proximal end relative to the first region of the tubular member.

The method of the present invention may further comprise a step of disposing the second linear member alone in a region on the side of the distal end relative to the second region of the tubular member.

According to a second aspect of the present invention, there is provided a catheter having a proximal end, a distal end and a tubular member defining an inner lumen extending between the proximal end and the distal end, comprising: a first resin layer arranged in a first region of the tubular member and consisting of a first resin material disposed in a dense spiral or mesh and a second resin material disposed in a sparse spiral or mesh; and a second resin layer arranged in a second region of the tubular member and consisting of the second resin material disposed in a dense spiral or mesh and the first resin material disposed in a sparse spiral or mesh.

The catheter of the present invention may further comprise a resin layer arranged in an intermediate region between the first region and the second region of the tubular member and consisting of the first resin material disposed in a spiral or mesh of a disposing density intermediate between the disposing densities in the first region and the second region and the second resin material disposed in a spiral or mesh in a disposing density intermediate between the disposing densities in the first region and the second region.

In the catheter of the present invention, the first region, the intermediate region and the second region are arranged in the order mentioned as viewed from, for example, the proximal end of the tubular member.

In the catheter of the construction described above, it is possible for a resin layer consisting of the first resin material alone to be arranged in a region on the side of the proximal end relative to the first region of the tubular member. Also, in the catheter of the construction described above, it is possible for a resin layer formed of the second resin material alone to be arranged in a region on the side of the distal end relative to the second region of the tubular member.

In the catheter of the present invention, it is possible for second resin layers consisting of the second resin material disposed in a dense spiral or mesh and the first resin material disposed in a sparse spiral or mesh to be arranged in two second regions on the sides of the proximal end and the distal end, respectively, relative to the first region of the tubular member. In this case, the second region on the side of the proximal end, the first region and the second region on the side of the distal end are arranged in the order mentioned as viewed from the proximal end of the tubular member.

In the catheter of the construction described above, it is possible for a resin layer consisting of the first resin material alone to be arranged in a region on the side of the proximal end relative to the second region on the side of the proximal end. Also, in the catheter of the construction described above, it is possible for a resin layer formed of the second resin material alone to be arranged in a region on the side of the distal end relative to the second region on the side of the distal end.

In the catheter of the present invention, it is desirable for the first resin material to have a flexural rigidity higher than that of the second resin material.

In the catheter of the present invention, it is possible for the first and second resin layers to be formed of the first resin material and the second resin material that are melted at least partially so as to be mixed or fused and, then, solidified. In this case, it is possible for at least one of the first and second resin materials to be melted partially so as to retain the skeleton thereof.

In the catheter of the present invention, it is possible for the first and second resin layers to be formed in a region except the distal end portion of the tubular member.

The catheter of the present invention may further comprise a reinforcing layer made of a metal on the tubular member. It is desirable for the reinforcing layer to be consisted of a braided body of a metal wire or a metal ribbon. The catheter of the present invention may further comprise a low friction layer on the inner surface of the tubular member. The catheter of the present invention may further comprise an outer layer formed on the first and second resin layers.

Another method for manufacturing a catheter of the present invention comprises steps of: preparing a first linear member made of a first resin material, a second linear member made of a second resin material, and a mandrel; disposing the first linear member in the form of a dense spiral or mesh on a first region of the mandrel and in the form of a sparse spiral or mesh on a second region of the mandrel; disposing the second linear member in the form of a sparse spiral or mesh on the first region of the mandrel and in the form of a dense spiral or mesh on the second region of the mandrel; melting at least partially the first and second linear members disposed on the mandrel so as to mix or fuse the first and second members; solidifying these first and second linear members; and drawing out the mandrel, thereby forming a catheter comprising a resin layer having a proximal end and a distal end, and defining an inner lumen extending between the proximal end and the distal end.

Another catheter of the present invention comprises a resin layer having a proximal end and a distal end, and defining an inner lumen extending between the proximal end and the distal end, wherein a first region of the resin layer consists of a first resin layer constituted by a first resin material formed into a dense spiral or mesh and a second resin material formed into a sparse spiral or mesh, and a second region of the resin layer consists of a second resin layer constituted by the second resin material formed into a dense spiral or mesh and the first resin material formed into a sparse spiral or mesh.

According to the present invention, two kinds of resin materials differing from each other in properties are used for adjusting the disposing densities so as to provide a catheter having a flexural rigidity gradually diminished from the proximal end toward the distal end. The particular catheter exhibits excellent following capability, safety and kink resistance.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed descrip

FIG. 4 shows a manufacturing step of the catheter of the present invention;

FIG. 5 shows a manufacturing step of the catheter of the present invention;

DETAILED DESCRIPTION OF THE INVENTION

The catheter and the manufacturing method thereof according to preferred embodiments of the present invention will now be described with reference to the accompanying drawings.

Figure 1:
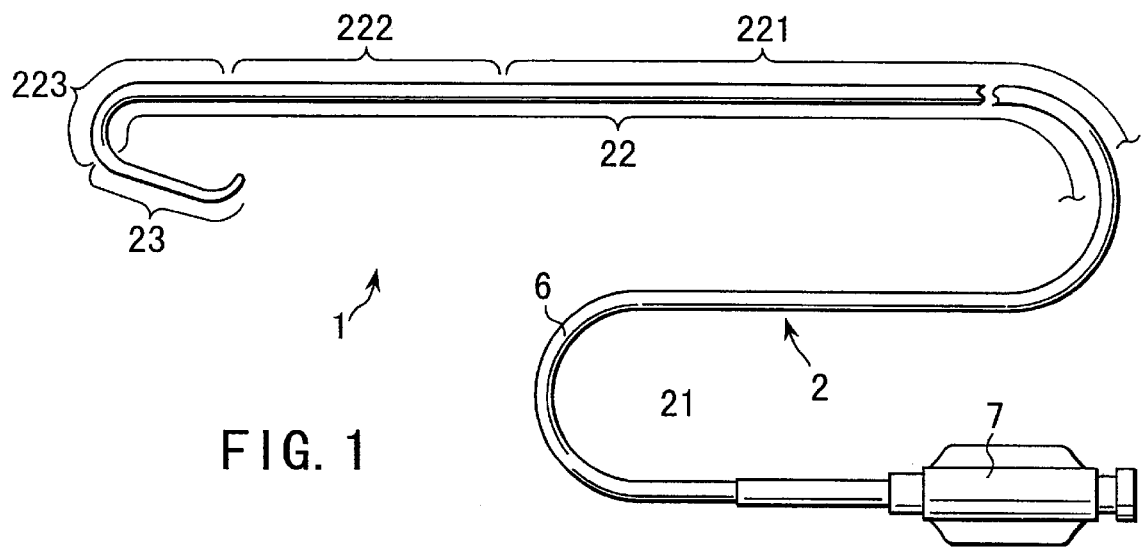
- FIG. 1 is a plan view showing a catheter according to an embodiment of the present invention.
Figure 2:
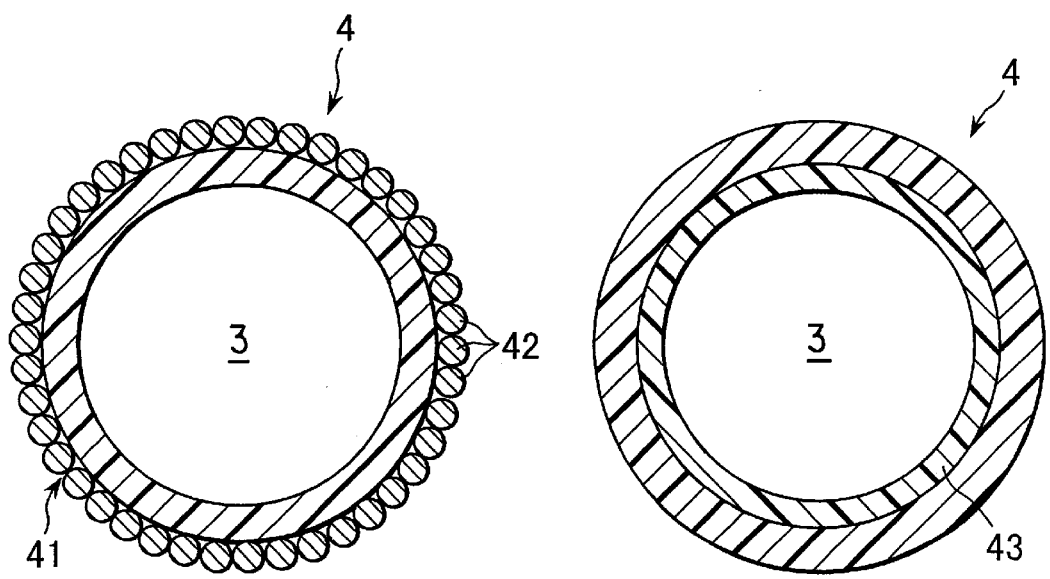
FIG. 2 is a cross sectional view showing a base tube included in the catheter of the present invention.
Figure 3:
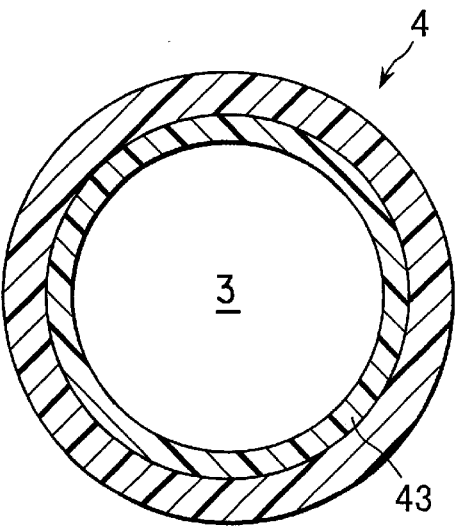
FIG. 3 is a cross sectional view showing another example of a base tube used in the catheter of the present invention.

FIG. 1 is a plan view showing the entire intracatheter according to an embodiment of the present invention. FIGS. 2 and 3 are cross sectional views each showing a base tube used in the catheter of the present invention shown in FIG. 1. Further, FIGS. 4 to 7 show the manufacturing process of the catheter of the present invention.

As shown in FIG. 1, a catheter 1 has a catheter main body 2. In this example, the catheter main body 2 is divided for the sake of convenience in description into a main portion 22 and a distal end portion 23 from the side of the proximal end 21. Further, the main portion 22 is divided into a first region 221, an intermediate region 222, and a second region 223 from the side of the proximal end 21.

As shown in FIGS. 2 to 7, an inner lumen 3 extending from the proximal end 21 to the distal end is formed within the catheter main body 2. When the catheter 1 is inserted into a blood vessel, a guide wire is inserted into the inner lumen 3. The inner lumen 3 is also used as a passageway of a contrast medium or a medical solution.

Figure 6:
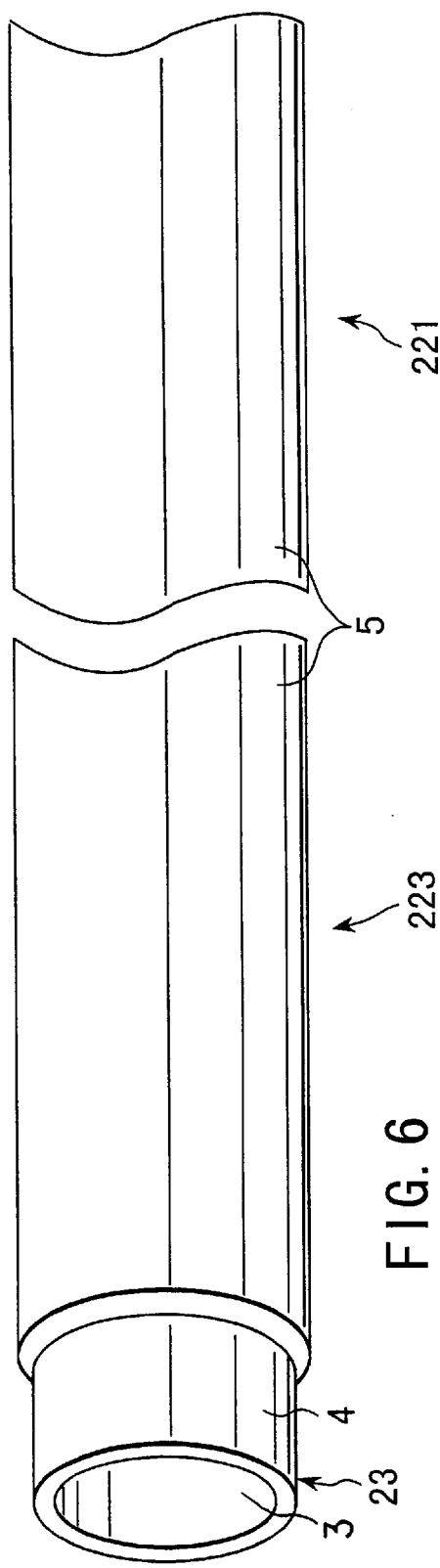
FIG. 6 shows a manufacturing step of the catheter of the present invention.
Figure 7:
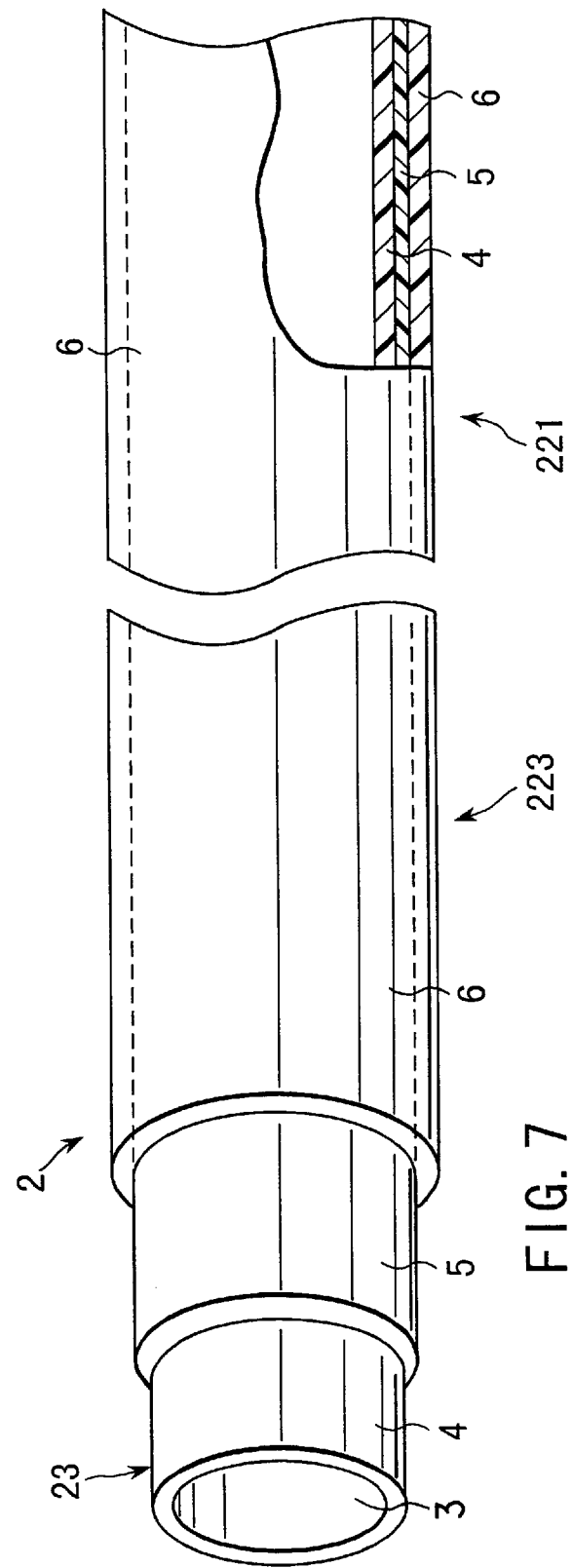
FIG. 7 shows a manufacturing step of the catheter of the present invention.

As shown in FIG. 6, the main portion 22 of the catheter main body 2 comprises a base tube (inner layer) 4 as a tubular member and a resin layer 5 surrounding the base tube 4. As shown in FIG. 7, it is possible to form as desired an outer layer 6 surrounding the resin layer 5. The distal end portion 23 of the catheter main body 2 consists of the base tube 4 alone and does not include the resin layer 5. Alternatively, it is possible for the distal end portion 23 to consist of the base tube 4 and the outer tube 6.

As shown in FIG. 1, a hub 7 is mounted to the proximal end 21 of the catheter main body 2. The hub 7 acts as an insertion port of a guide wire into the inner lumen 3 and as an injection port of a medical solution or the like into the inner lumen 3, and also functions as a gripper when the catheter is operated.

In the present invention, the resin layer 5 is formed by using a first linear member (strand or filament) 51 made of a first resin material and a second linear member (strand or filament) 52 made of a second resin material. Each of the first linear member 51 and the second linear member 52 is made of a resin material, particularly, a thermoplastic resin. However, these first and second linear members 51 and 52 differ from each other in properties, e.g., physical properties such as the flexural rigidity (flexibility), surface hardness, elongation, tensile strength, shear strength, Izod impact strength, flexural modulus of elasticity, flexural strength, dielectric constant, softening point, melting point, specific gravity, water absorption, and hydrophilic property, although not limited to those properties. In addition, the first and second resin materials differ from each other in the above mentioned properties. In this embodiment, the first resin material has a flexural rigidity higher than that of the second resin material, and thereby, the first linear member 51 has a flexural rigidity higher than that of the second linear member 52. In other words, the first linear member 51 is less flexible than the second linear member 52.

The resin layer 5 comprises a first resin layer formed by arranging the first linear member 51 in a high density and the second linear member 52 in a low density and a second resin layer formed by arranging the first linear member 51 in a low density and the second linear member 52 in a high density. Also, it is possible to form as desired a resin layer consisting of the first linear member 51 arranged in a density intermediate between the densities in the first region and the second region and the second linear member 52 arranged in a density intermediate between the densities in the first region and the second region in an intermediate region between the first region and the second region. In this case, the arranging density of the first linear member 51 is substantially equal to that of the second linear member 52 in some portion of the intermediate region, though the arranging densities of the first and second linear members are not particularly limited. The first linear member 51 and the second linear member 52 are arranged in the form of a spiral or mesh around the outer surface of the base tube 4. The case of spirally winding the first and second linear members will be described first.

In the embodiment shown in FIGS. 4 and 5, the first linear member 51 and the second linear member 52 are wound around the outer surface of the base tube 4 in opposite directions. In this embodiment, the first linear member 51 and the second linear member 52 are wound in a high density and a low density, respectively, in the first region 221 of the main portion 22 of the catheter main body 2. In the second region 223, however, the first and second linear members 51 and 52 are wound in a low density and a high density, respectively. In the intermediate region 222 between the first region 221 and the second region 223, the first linear member 51 and the second linear member 52 are wound in substantially the same density. The arranging densities of the first linear member 51 and the second linear member 52 can be changed continuously over the first, intermediate and second regions or can be changed stepwise in more than three steps.

In this embodiment, the resin layer 5 is not formed in the distal end portion 23 of the catheter main body 2. In this case, it is possible for a part of the distal end portion 23 that does not include the distal end to be wound with only one of the first linear member 51 and the second linear member 52, with the remaining part including the distal end not wound with any of the first and second linear members 51 and 52. Also, if the second linear member 52 has a very small rigidity (or highly flexible), it is possible to wind the second linear member 52 over the entire distal end portion 23 including the distal end. Incidentally, it is possible to wind the first linear member 51 alone in a region on the side of the proximal end relative to the first region 221 of the catheter main body 2, though the first linear member 51 wound in this fashion is not shown in the drawing. In this fashion, regions where the first linear member 51 and the second linear member 52 partially differ from each other in the arranging density are formed continuously in the longitudinal direction of the catheter main body 2.

It is desirable for the first linear member 51 and the second linear member 52, which may be left in the wound state, to be thermally melted to achieve mixing or fusing, followed by solidifying by cooling to form a resin layer. If the first linear member 51 and the second linear member 52 are melted and, then, solidified, a flat resin layer 5 is formed to cover the outer surface of the base tube 4, as shown in, for example, FIG. 6. Incidentally, it is possible for the first linear member 51 and the second linear member 52 not to be melted completely so as to retain the skeletons of the original linear members to some extent. The first linear member 51 and the second linear member 52 as wound around the base tube 4 tend to be moved during use of the catheter. On the other hand, the resin layer formed by melting and solidifying the first linear member 51 and the second linear member 52 is not moved during use of the catheter, with the result that the flexural rigidity, flexibility, etc., are stabilized in each part of the catheter main body 2.

In the catheter 1 of the construction described above, the flexural rigidity of the catheter main body 2 is gradually diminished in the order of the first region 221, the intermediate region 222 and the second region 223. Therefore, the first region 221 has a sufficient rigidity so as to exhibit excellent pushability and torque transmitting capability. Also, if the flexural rigidity of the catheter main body 2 is diminished toward the distal end, excellent following capability and kink resistance can be obtained, which gives very small stimulus to the inner wall of the blood vessel. In addition, since the resin layer 5 is not formed on the distal end portion 23 or on the side of the distal end of the distal end portion 23, the distal end portion 23 is highly flexible. As a result, it is possible to prevent damaging the inner wall of the blood vessel (or body cavity) into which the catheter 1 is inserted, leading to a very high safety.

The resin material of the first linear member 51 and the second linear member 52 includes, for example, thermoplastic resins such as polyesters such as polyethylene terephthalate and polybutylene terephthalate, polyolefins such as polyethylene and polypropylene, polyvinyl chloride, polyamide, polystyrene, thermoplastic polyurethane, polycarbonate, ABS resin, acrylic resin, polymethyl methacrylate (PMMA), polyacetal (PA), polyarylate, polyoxymethylene (POM), high tensile polyvinyl alcohol, fluoroplastics, polyvinylidene fluoride (PVdF), polytetrafluoroethylene, ethylene-saponified vinyl acetate (EVOH), polysulfone, polyether sulfone, polyether ketone, polyphenylene oxide, and polyphenylene sulfide; thermoplastic elastomers such as polyamide elastomer, polyester elastomer, polyurethane elastomer, and polyolefin elastomer; polymer alloys containing any of these polymers; and a combination of at least two of these materials.

Where the first linear member 51 and the second linear member 52 are melted, it is desirable to select compatible materials for forming these first and second linear members 51 and 52. Combinations of compatible resin materials used in the present invention include, for example, a combination or polyurethane and polyamide, a combination of polyamide and polyamide elastomer, a combination of polyethylene or polypropylene and polyolefin elastomer, a combination of polyethylene terephthalate and polyester elastomer, a combination of polyurethane and polyester elastomer, and a combination of a high plasticizing polyvinyl chloride and a low plasticizing polyvinyl chloride.

It is desirable for the first linear member 51 to exhibit a flexural modulus of elasticity of 8,000 to 25,000 $kg/cm^2$, preferably 10,000 to 15,000 $kg/cm^2$. Also, it is desirable for the second linear member 52 to exhibit a flexural modulus of elasticity of 100 to 4,000 $kg/cm^2$, preferably 300 to 2,500 $kg/cm^2$. Where the flexural modulus of elasticity of the first linear member 51 is set at 1, it is desirable for the flexural modulus of elasticity of the second linear member 52 to be 0.004 to 0.5, preferably 0.02 to 0.17. By setting the flexural modulus of elasticity to fall within the range noted above, it is possible to improve the pushability, the torque transmitting capability, the following capability and the kink resistance in good balance.

The first linear member 51 and the second linear member 52 may be formed of a single fiber or a combined fiber prepared by twisting single fibers.

The first linear member 51 and the second linear member 52 may be circular in cross section or may be formed of a ribbon having a flat cross section. In the embodiment shown in FIG. 5, a ribbon is used for forming each of the first linear member 51 and the second linear member 52. Also, it is possible for the first linear member 51 and the second linear member 52 to be different from each other in the cross sectional shape.

Where the first linear member 51 and the second linear member 52 are circular in cross section, it is desirable for each of these linear members to have a diameter of 0.01 to 0.5 mm, preferably 0.03 to 0.3 mm. Where the first linear member 51 and the second linear member 52 are formed of ribbons, it is desirable for the ribbon constituting each of these linear members to have a width of 0.03 to 5 mm and a thickness of 0.03 to 0.2 mm.

The diameter or width of each of these first and second linear members 51 and 52 need not be constant over the entire length of the catheter, and may be changed continuously or stepwise. For example, it is possible for the diameter or width of the first linear member 51 having a high rigidity to be diminished from the proximal end toward the distal end of the catheter main body 2, while increasing the diameter or width of the second linear member 52 from the proximal end toward the distal end of the catheter main body 2, so as to further change the densities of the first and second linear members 51 and 52.

The ratio of the first linear member 51 to the second linear member 52 in the first region 221 in terms of the areal ratio or weight ratio of the first linear member 51 to the second linear member 52 should desirably fall within a range of between 1:0.1 and 1:0.95, preferably between 1:0.3 and 1:0.7.

The ratio of the first linear member 51 to the second linear member 52 in the second region 223 in terms of the areal ratio or weight ratio of the first linear member 51 to the second linear member 52 should desirably fall within a range of between 0.1:1 and 0.95:1, preferably between 0.3:1 and 0.7:1.

In the construction shown in the drawing, the inner diameter and the outer diameter of each of the base tube 4 and the outer layer 6 are set constant. However, these inner diameter and outer diameter may be changed in the longitudinal direction of the catheter main body 2. It is also possible for these sizes to be changed partially.

For example, it is possible for the outer diameter of the outer layer 6 to be gradually diminished toward the distal end of the catheter main body 2 or for the inner diameter of the base tube 2 to be gradually increased toward the distal end of the catheter main body 2 at the boundary region at which the relationship of densities of the first linear member 51 and the second linear member 52 of the resin layer 5 are changed or at the boundary region between the distal end portion 23 and the second region 223. In this construction, the thickness of the base tube 4 or the outer layer 6 is gradually diminished toward the distal end and, thus, the rigidity (flexural rigidity) of the catheter main body 2 is decreased continuously so as to improve the kink resistance.

The lengths of the first region 221, the intermediate region 222 and the second region 223 are not particularly limited. In a intracatheter, particularly an angiography catheter, as shown in FIG. 1, it is desirable for each of the second region 223 and the intermediate region 222 to have a length of 50 to 300 mm. On the other hand, the length of the first region 221, which differs depending on, for example, the kind of the catheter, is not particularly limited.

The other members constituting the catheter of the present invention will now be described.

The base tube 4 is made of a flexible material including, for example, polyolefin such as polypropylene, polyethylene, and ethylene-vinyl acetate copolymer, polyamide, polyesters such as polyethylene terephthalate (PET) and polybutylene terephthalate (PBT), polyurethane, polyvinyl chloride, polystyrene-based resins, fluoroplastics such as polytetrafluoroethylene and ethylene-tetrafluoroethylene copolymer, polyimide, and various elastomers such as polyamide elastomer, polyester elastomer, polyurethane elastomer, polystyrene elastomer, fluorinated elastomer, silicone rubber and latex rubber. It is also possible to use at least two of these compounds in combination.

The typical polyamide elastomer is a block copolymer consisting of a hard segment such as an aliphatic or aromatic polyamide including, for example, nylon 6, nylon 64, nylon 66, nylon 610, nylon 612, nylon 46, nylon 9, nylon 11, nylon 12, N-alkoxymethyl-modified nylon, hexamethylene diamine-isophthalic acid condensation polymer, or methaxyloyl diamine-adipic acid condensation polymer, and a soft segment consisting of a polymer such as polyester or polyether. It is also possible to use a polymer alloy (polymer blend), a graft copolymer or a random copolymer consisting of polyamide and a highly flexible resin, a softened polyamide softened with a plasticizer. Further, it is possible to use mixture thereof.

The typical polyester elastomer used in the present invention is a block copolymer between a saturated polyester such as polyethylene terephthalate or polybutylene terephthalate and a polyether or a polyester. It is also possible to use a polymer alloy or a softened saturated polyester prepared by softening with a plasticizer. Further, a mixture of these materials can also be used as the polyester elastomer.

The base tube 4 shown in the drawings is of a single layer structure. However, the base tube 4 may also be formed of a plurality of layers.

Specifically, a reinforcing layer 41 is formed on the outer surface of the base tube 4, as shown in FIG. 2. It is desirable for the reinforcing layer 41 to be formed of a braided body constituted by a metal wire 42 or a metal ribbon made of, for example, a steel wire or a stainless steel wire. It is also possible to use a coil made of a hard material such as a metal or to use a slit tube as the reinforcing layer. The reinforcing layer may also be arranged on the inner surface of the base tube or may be buried within the base tube. Further, the reinforcing layer may be arranged between the resin layer 5 and the outer layer 6 unlike the construction shown in FIG. 2.

The reinforcing layer 41 may be formed in an arbitrary position in the longitudinal direction of the catheter main body. For example, the reinforcing layer 41 may be formed over the entire length of the catheter main body 2, or may be formed over the entire length of the catheter main body 2 except the distal end portion 23, or may be formed over the entire length of the catheter main body 2 except the distal end portion 23 and a part of or entire region of the second region 223. In short, the forming position of the reinforcing layer 41 may be determined appropriately in view of the use and required properties of the catheter.

As shown in FIG. 3, a low friction layer 43, which is exposed to the inner lumen 3, is formed on the inner surface of the base tube 4. The low friction layer 43 can be formed of any material as far as the friction of the layer 43 exposed to the inner lumen 3 can be suppressed. For example, it is possible to use polytetrafluoroethylene, perfluoroalkoxy resin, polyethylene or polyimide for forming the low friction layer 43. The low friction layer 43 can be formed by, for example, a dip coating method.

The position of the low friction layer 43 in the longitudinal direction of the catheter main body is not particularly limited, though it is desirable to form the low friction layer 43 over the substantially entire length of the catheter main body 2. It is also possible to use the material of the low friction layer for forming the base tube 4.

A guide wire inserted into the inner lumen 3 is brought into a sliding contact with the low friction layer 43. In this case, the sliding resistance is lowered so as to facilitate the operation for inserting the catheter 1 into a blood vessel along the guide wire moving forward of the catheter 1 and the operation for drawing the guide wire from the catheter 1.

The material used for the outer layer 6, which is formed as required, can be the same material as used for the base tube 4. It is desirable for the material of the outer layer 6 to have a Shore D hardness of about 40 to 80. As shown in FIG. 7, it is possible to form the outer layer 6 not to cover the distal end portion 23 and the distal end portion of the second region 223 of the catheter main body 2. In this case, the change in rigidity (flexibility) in the axial direction of the catheter main body 2 is made more moderate so as to improve the following capability and the kink resistance.

In the present invention, the balance of rigidity (flexibility) in each region of the catheter main body 2 depends mainly on the construction of the resin layer 5. Therefore, the present invention is advantageous in that the materials of the base tube 4 and the outer layer 6 are not restricted in terms of the physical properties (particularly, rigidity and hardness) and, thus, can be selected from a wide range.

In order to permit the position of the catheter main body 2 to be visually recognized under fluororoentgenography during use of the catheter, it is possible to allow the base tube 4 (or the layer constituting the tube 4) or the outer layer 6 to contain an X-ray contrast medium such as a metal powder of platinum, gold, silver, tungsten, or an alloy thereof as well as barium sulfate, bismuth oxide or a coupling compound thereof. Such an X-ray contrast medium may be contained in one or both of the linear members 51 and 52.

In the present invention, it is desirable for the outer surface of the catheter main body 2 to be covered with a hydrophilic (or water soluble) high molecular weight material. In this case, when the outer surface of the catheter main body 2 is brought into contact with blood or a physiological saline, the friction coefficient is lowered and lubricity is imparted to the outer surface of the catheter main body 2 so as to further improve the sliding properties of the catheter main body 2. As a result, it is possible to further improve the pushability, the following capability, the kink resistance and the safety of the catheter.

The hydrophilic high molecular weight material used in the present invention includes natural or synthetic high molecular weight materials and derivatives thereof. Particularly, it is desirable to use a cellulose-based high molecular weight material such as hydroxypropyl cellulose, a polyethleneoxide-based high molecular weight material such as polyethylene glycol, a maleic anhydride-based high molecular weight material such as a maleic anhydride copolymer like methyl vinyl ether-maleic anhydride copolymer, an acrylamide-based high molecular weight material such as polyacrylamide, and a water-soluble nylon such as AQ-nylon P-70 manufactured by Toray Inc. because a low friction coefficient can be obtained stably in these materials. It is also possible to use a derivative of the water-soluble high molecular weight material that is made insoluble, as far as the molecular chain of the derivative has a degree of freedom and the derivative is capable of containing water.

In order to cover the outer surface of the catheter main body 2 with the hydrophilic high molecular weight material, it is desirable for the hydrophilic high molecular weight material to form a covalent bond with the reactive functional group present in or introduced into the outer layer 6 or the surface of the outer layer 6 (or the resin layer 5 or the surface of the resin layer 5 where the outer layer 6 is not formed). In this case, it is possible to obtain a sustainable lubricating surface.

Any kind of the reactive functional group can be used as far as the functional group reacts with the high molecular weight material to form a chemical bond or crosslinkage so as to be fixed. The specific reactive functional groups used in the present invention include, for example, diazonium group, azide group, isocyanate group, acid chloride group, acid anhydride group, imino carbonate group, amino group, carboxyl group, epoxy group, hydroxyl group, and aldehyde group. Particularly, it is desirable to use isocyanate group, amino group, aldehyde group and epoxy group as the reactive functional group.

Figure 16:
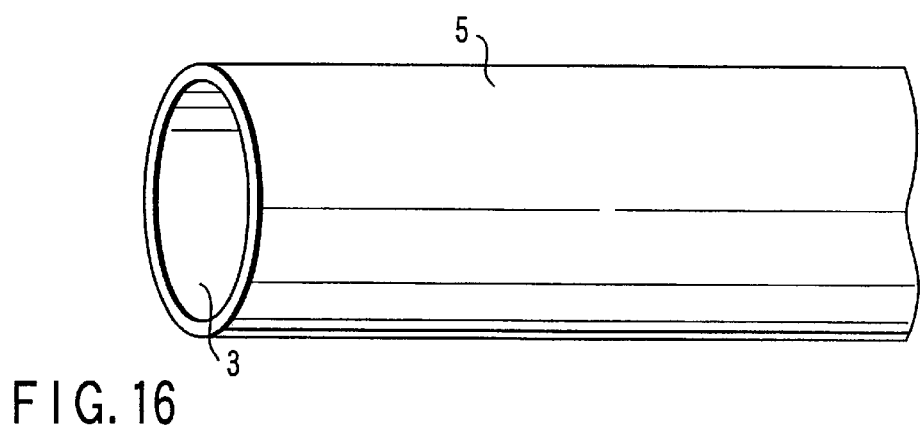
FIG. 16 is a plan view showing yet another example of the catheter of the present invention.

The catheter of the present invention suffices if only it comprises the resin layer 5 formed by using at least the first linear member 51 and the second linear member 52. A catheter of an embodiment of the present invention comprises a resin layer 5 having a proximal end and a distal end and defining an inner lumen extending between the proximal end and the distal end without the aforementioned base tube 4, as shown in FIG. 16.

Next, a method for manufacturing the catheter of the present invention will now be described. In the first step, the base tube 4 is manufactured by the ordinary method. As described previously, it is possible for the base tube 4 to include the reinforcing layer 41 and the low friction layer 43.

The first linear member 51 is spirally wound around the outer surface of the base tube 4. To be more specific, the first linear member 51 is provided from a linear member supply source. On the other hand, the base tube 4 is moved in its axial direction relative to the linear member supply source and is relatively rotated around its own axis so as to allow the linear member 51 to be continuously wound around the outer surface of the base tube 4. For example, the winding of the first linear member 51 is started at the boundary region between the distal end portion 23 and the second region 223, and the base tube 4 is rotated at a predetermined speed. The moving speed of the base tube 4 in its axial direction is gradually decreased in the winding positions in the second region 223, the intermediate region 222 and the first region 221. As a result, the winding density of the first linear member 51 is increased from the distal end portion toward the proximal end portion, as shown in FIG. 4. Then, the second linear member 52 is spirally wound around the base tube 4 having the first linear member 51 wound around it in advance by using an apparatus equal to the apparatus described above. For example, the winding of the second linear member 52 is started at the boundary region between the distal end portion 23 and the second region 223, and the base tube 4 is rotated in the opposite direction at a predetermined rotating speed. Under this condition, the moving speed of the base tube 4 in its axial direction is increased stepwise in the second region 223, the intermediate region 222 and the first region 221 in the order mentioned. In this fashion, the winding density of the second linear member 52 is decreased from the distal end portion toward the proximal end portion, as shown in FIG. 5.

The first linear member 51 and the second linear member 52 thus wound around the base tube 4 are melted by heating. When the molten materials are solidified by cooling, the flat resin layer 5 is formed on the outer surface of the base tube 4, as shown in FIG. 6.

The heating can be achieved by, for example, allowing the base tube 4 having the first linear member 51 and the second linear member 52 wound around the outer surface to pass through a heat die having an opening sized substantially equal to a desired outer diameter. Alternatively, it is possible to have the first linear member 51 and the second linear member 52 covered with a heat shrinkable tube made of, for example, a fluoroplastics-based resin. In this case, the heat shrinkable tube is thermally shrunk by heating. After the heat treatment, the heat shrinkable tube may be removed. However, if left unremoved, the heat shrinkable tube can be used as the outer layer 6.

The heating conditions are determined appropriately in view of the materials, particularly the melting points, of the base tube 4, the first linear member 51 and the second linear member 52. In general, the heating should desirably be performed at 100 to 500° C. for 1 to 15 minutes.

During the heating, it is possible for the first linear member 51 and the second linear member 52 to be melted completely and to be solidified in a uniformly mixed or fused state. It is also possible for the first linear member 51 and the second linear member 52 to be melted at least partially but not fully mixed or fused such that at least one of these linear members retains the skeleton, that is, retains the shape before the melting to some extent in the solidified state after cooling. In an embodiment of the present invention, one of the first linear member 51 and the second linear member 52, which has a lower melting point, is melted, and the other linear member having a higher melting point retains the original linear shape in part. In this case, the molten resin enters the clearance of the linear member retaining the original shape so as to be solidified.

Where the resin material forming the first linear member 51 has a melting point $T_1$ and the resin material forming the second linear member 52 has a melting point $T_2$, it is desirable for the difference $\Delta T$ between $T_1$ and $T_2$, i.e., $\Delta T=|T_1-T_2|$, to be 3 to 120° C., preferably 5 to 70° C. The difference $\Delta T$ of this level makes it possible to obtain easily the particular molten state described above.

In the present invention, it is possible to use an adhesive or a solvent for fixing the first linear member 51 and the second linear member 52 to the base tube 4.

After formation of the resin layer 5, the outer surface of the resin layer 5 is covered with the outer layer 6, as desired. The resin layer 5 can be covered with the outer layer 6 by various methods. For example, it is possible to use an adhesive or a solvent for fixing the outer layer 6 to the base tube 4 having the resin layer 5 formed thereon. It is also possible to apply a thermal fusion or a high frequency fusion of the outer layer 6 to the base material 4 having the resin layer 5 formed thereon. It is also possible to insert the base tube 4 having the resin layer 5 formed thereon into the outer layer 6 expanded by heating or by using a solvent, followed by shrinking the outer layer 6. Further, it is possible to extrude the outer layer 6 onto the base tube 4 having the resin layer 5 formed thereon, followed by cooling the extrudate for solidification, or to coat the resin layer 5 formed on the base tube 4 with a solution of the outer layer material, followed by evaporating the solvent to form the outer layer 6.

After the outer surface of the outer layer 6 (or the resin layer 5 where the outer layer 6 is not formed) is covered with a hydrophilic high molecular weight material, as desire, the hub 7 is mounted to the proximal end 21 of the catheter main body 2 so as to complete preparation of the catheter 1 of the present invention.

Figure 19:
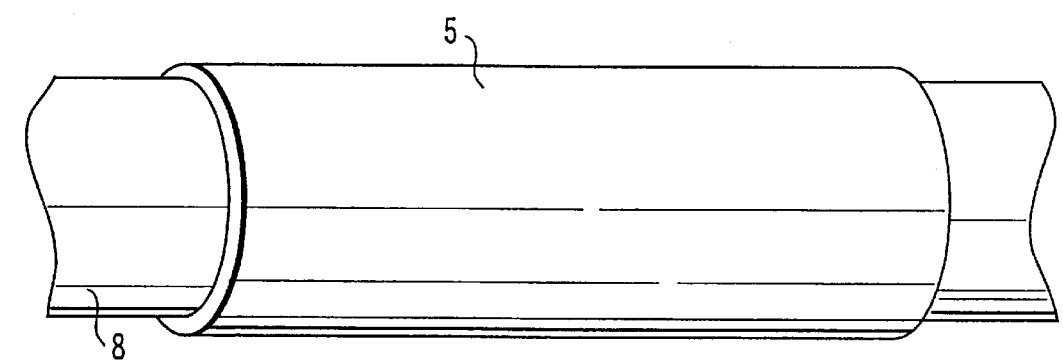
FIG. 19 shows a manufacturing step of the catheter shown in FIG. 16.

It is possible to use another method for manufacturing a catheter of the present invention in which the first linear member 51 and the second linear member are wound around a mandrel in place of the base tube 4 and finally draw out the mandrel so as to form the catheter. In this method, the catheter main body 2 that does not include the base tube 4 can be obtained. Such a method for manufacturing the catheter is described with referring to FIGS. 17, 18 and 19.

A mandrel 8 used in this method includes a metal wire made of, for example, copper, aluminum, gold, silver and stainless steel. In order to make it easy to draw out the mandrel finally, a release agent such as silicone oil, fluorinated oil, liquid paraffin or paraffin wax may be applied on the outer surface of the mandrel.

Figure 17:
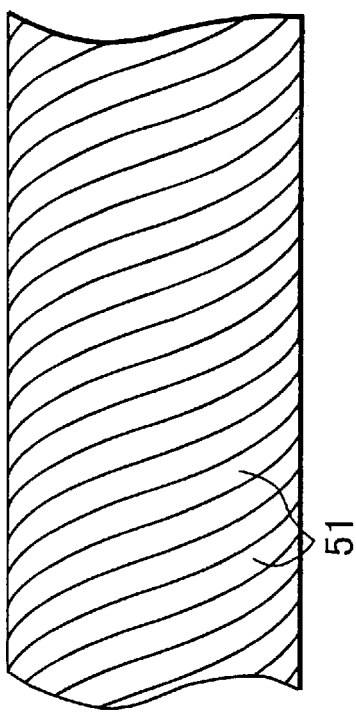
FIG. 17 shows a manufacturing step of the catheter shown in FIG. 16.
Figure 17:
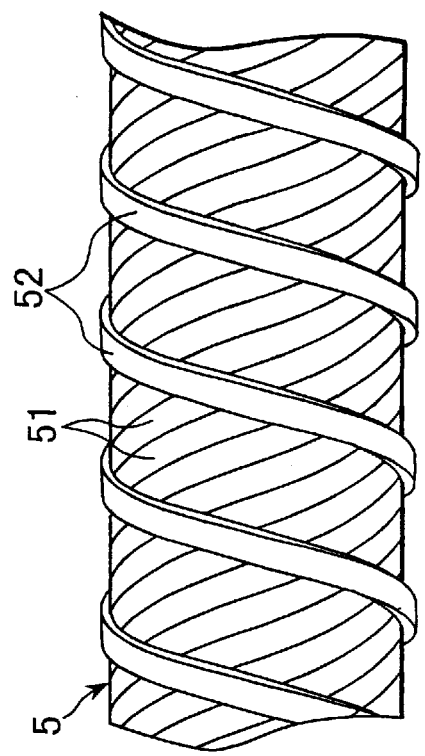
Figure 17:
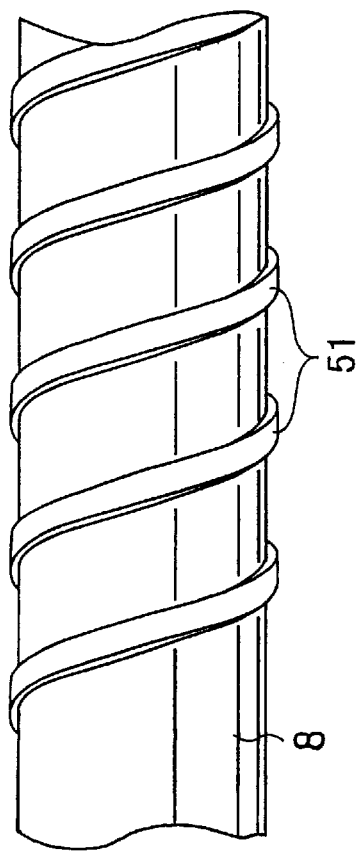

Next, the first linear member 51 is spirally wound around the outer surface of the mandrel 8. To be more specific, the first linear member 51 is provided from a linear member supply source. On the other hand, the mandrel 8 is moved in its axial direction relative to the linear member supply source and is relatively rotated around its own axis so as to allow the linear member 51 to be continuously wound around the outer surface of the mandrel 8. For example, the winding of the first linear member 51 is started at the boundary region between the distal end portion 23 and the second region 223, and the mandrel 8 is rotated at a predetermined speed. The moving speed of the mandrel 8 in its axial direction is gradually decreased in the winding positions in the second region 223, the intermediate region 222 and the first region 221. As a result, the winding density of the first linear member 51 is increased from the distal end portion toward the proximal end portion, as shown in FIG. 17.

Figure 18:
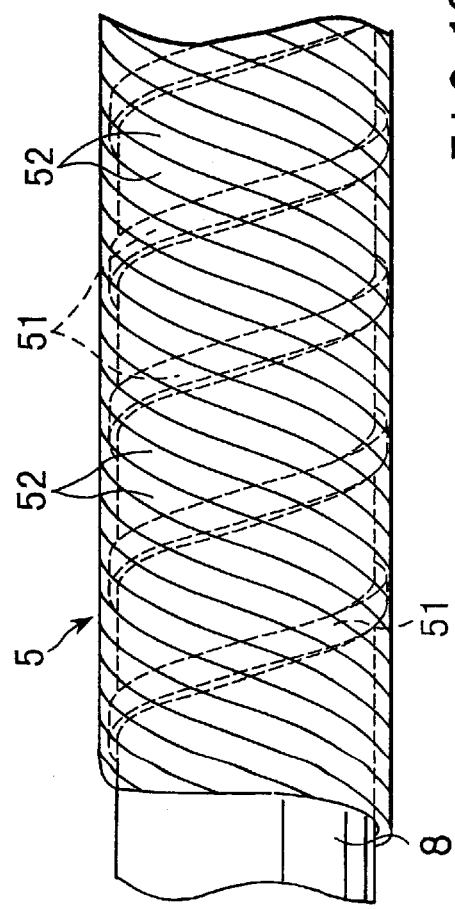
FIG. 18 shows a manufacturing step of the catheter shown in FIG. 16.

Then, the second linear member 52 is spirally wound around the mandrel 8 having the first linear member 51 wound around it in advance by using an apparatus equal to the apparatus described above. For example, the winding of the second linear member 52 is started at the boundary region between the distal end portion 23 and the second region 223, and the mandrel 8 is rotated in the opposite direction at a predetermined rotating speed. Under this condition, the moving speed of the mandrel 8 in its axial direction is increased stepwise in the second region 223, the intermediate region 222 and the first region 221 in the order mentioned. In this fashion, the winding density of the second linear member 52 is decreased from the distal end portion toward the proximal end portion, as shown in FIG. 18.

The first linear member 51 and the second linear member 52 thus wound around the mandrel 8 are melted by heating. When the molten materials are solidified by cooling, the flat resin layer 5 is formed on the outer surface of the mandrel 8. The heating method, the heating conditions, and the molten state of the linear members are like as the manufacturing method described above.

After formation of the resin layer 5, the outer surface of the resin layer 5 is covered with the outer layer 6, as desired. Methods of forming the outer layer 6 include those described with respect to the above manufacturing method.

Then, the mandrel 8 on which the resin layer 5 is formed is drawn out so as to obtain the shaped catheter main body 2. It is possible to use a method of drawing out the mandrel 8 in which the shaped resin layer 5 (and the outer layer 6) is fixed at one end and the mandrel 8 is drawn out from the other end. Alternately, the mandrel 8 may be stretched to diminish the diameter, in order to peeling off the shaped resin layer 5 from the mandrel 8. Then, the shaped resin layer 5 is fixed at one end and the mandrel 8 is drawn out from the other end. In order to make the mandrel 8 be stretched, the mandrel 8 may be fixed at one end and drawn from the other end, or the mandrel 8 may be drawn from the both ends. The extent of stretching given to the mandrel 8 may be about 10 to 30%, and generally set to about 15 to 25%.

In a manner as described above, a catheter main body 2 comprising a tubular resin layer 5 having a proximal end and a distal end and defining an inner lumen extending between the proximal end and the distal end is formed. A treatment to cover the outer surface of the outer layer 6 (or the resin layer 5 where the outer layer 6 is not formed) with a hydrophilic high molecular weight material may be performed, if desired. Then, the hub 7 is mounted to the proximal end 21 of the catheter main body 2 so as to manufacture the catheter 1 of the present invention. Incidentally, the treatment to cover with the hydrophilic high molecular weight material may be performed before the mandrel 8 is drawn out from the resin layer 5.

Needless to say, on the contrary to the above description with respect to the winding of the first and the second linear members 51 and 52, it is possible to start the winding of the first linear member 51 and/or the second linear member 52 from the proximal end portion of the catheter main body 2. It is also possible to change the rotating speed of the base tube 4 or the mandrel 8 in the winding positions of the second region 223, the intermediate region 222 and the first region 222, with the moving speed of the base tube 4 or the mandrel 8 in its axial direction set constant.

In the method of the present invention, it suffices to rotate and move in axial direction the base tube 4 or the mandrel 8 and the linear member supply source relative to each other. Therefore, it is possible to rotate the base tube 4 or the mandrel 8 while moving the linear member supply source in the axial direction of the base tube 4 or the mandrel 8. It is also possible to move the base tube 4 or the mandrel 8 in its axial direction while rotating the linear member supply source around the outer surface of the base tube 4 or the mandrel 8. Further, it is possible to fix the base tube 4 or the mandrel 8 and to rotate the linear member supply source around the outer surface of the base tube 4 or the mandrel 8 while moving the linear member supply source in the axial direction of the base tube 4 or the mandrel 8. Still further, these methods can be employed in combination.

If the first linear member 51 and the second linear member 52 are wound by the method described above, the first linear member 51 and the second linear member 52 can be arranged at desired winding densities by simply adjusting the relative moving speed or relative rotating speed of the base tube 4 or the mandrel 8 and the linear member supply source. In other words, the rigidity, etc., in each part of the catheter main body 2 can be adjusted at a desired balance so as to make it possible to manufacture easily a catheter having properties adapted for the purpose of use and the case of the disease to be treated.

It is also possible to manufacture easily a catheter having the winding densities of the first linear member 51 and the second linear member 52 continuously changed in the axial direction of the catheter main body 2 by simply changing continuously the relative moving speed or relative rotating speed of the base tube 4 or the mandrel 8 and the linear member supply source.

In the embodiment described above, the first linear member 51 is wound first, followed by winding the second linear member 52. However, the winding method of the two linear members is not particularly limited in the present invention. For example, it is possible to wind the first linear member 51 and the second linear member 52 simultaneously or with a predetermined time difference in the same or opposite directions. Alternatively, the second linear member 52 may be wound first, followed by winding the first linear member 51.

FIGS. 8 to 11 show another embodiment of the present invention in which the first linear member 51 and the second linear member 52 are arranged around the outer surface of the base tube 4 in a mesh configuration. The first linear member 51 is also made of a resin material having a flexural rigidity higher than that of the resin material forming the second linear member 52 in this embodiment, too. In other words, the first linear member 51 is less flexible than the second linear member 52.

Figure 8:
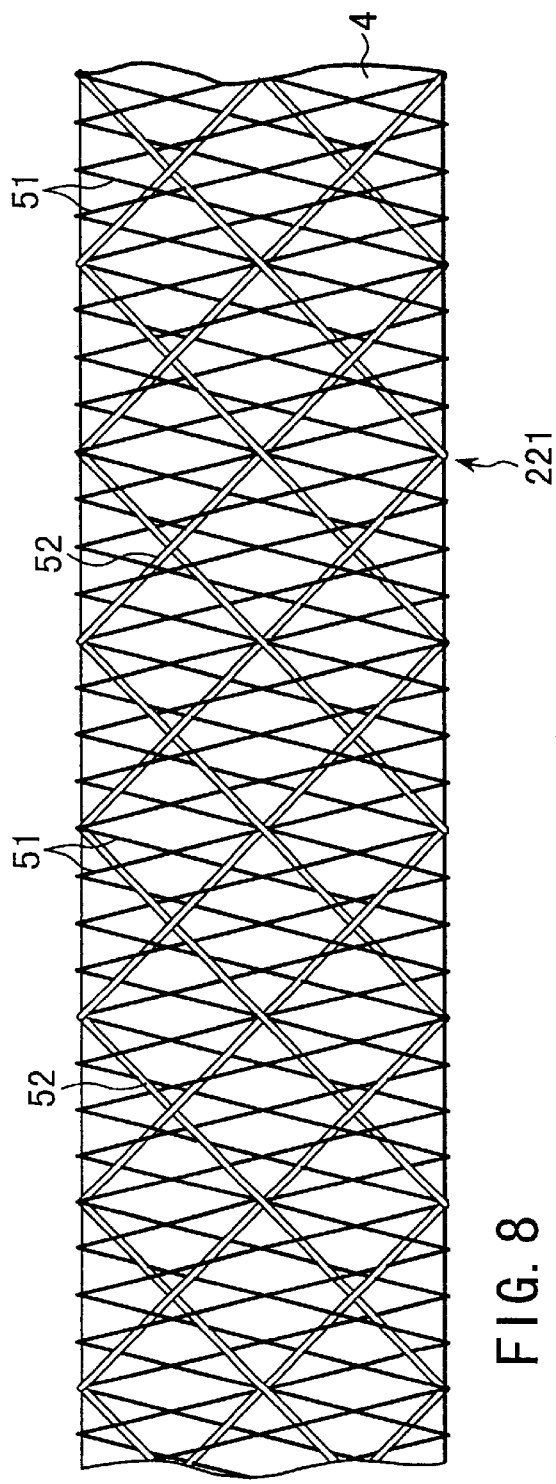
FIG. 8 is a plan view showing a winding pattern of the first linear member and the second linear member in a region on the side of the proximal end of the catheter of the present invention.
Figure 9:
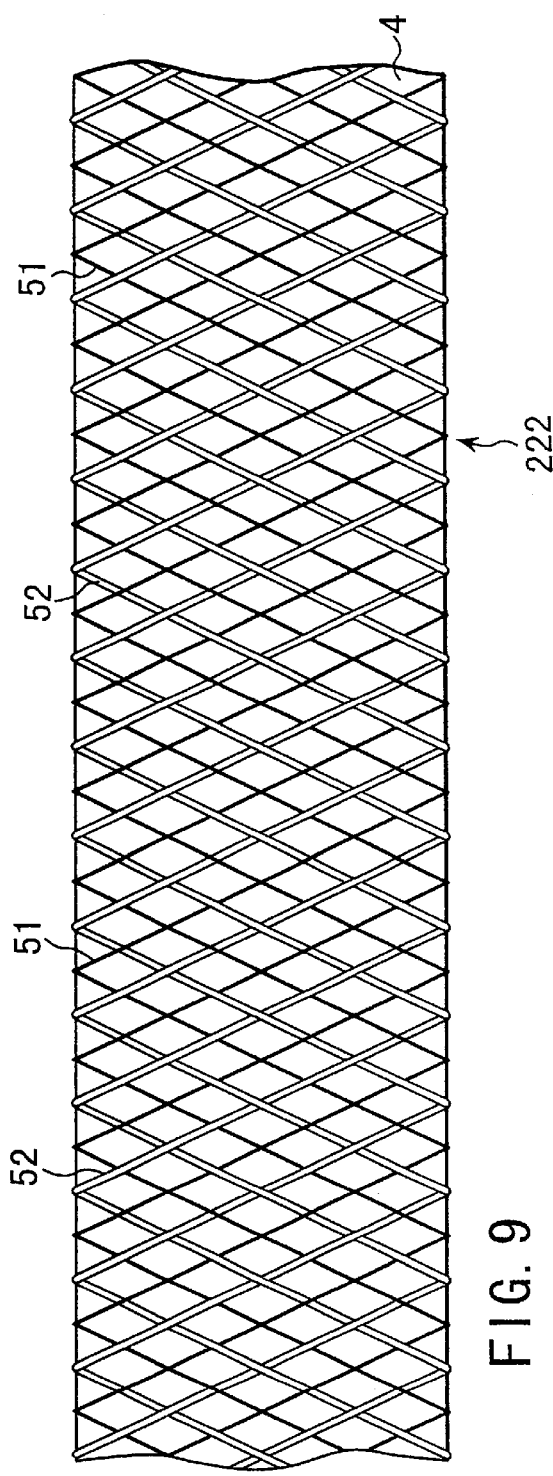
FIG. 9 is a plan view showing a winding pattern of the first linear member and the second linear member in an intermediate region of the catheter of the present invention.
Figure 10:
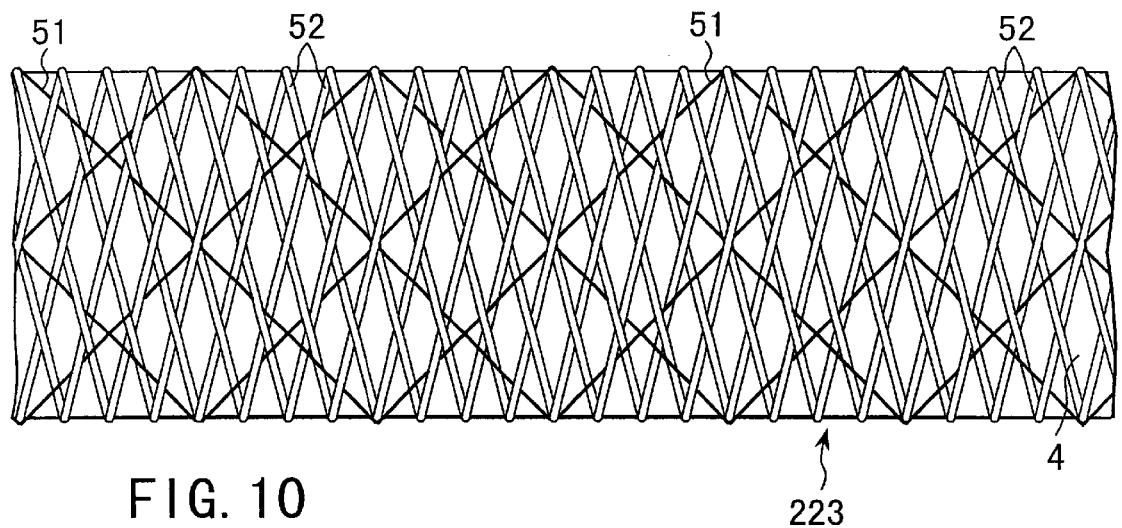
FIG. 10 is a plan view showing a winding pattern of the first linear member and the second linear member in a region on the side of the distal end of the catheter of the present invention.

FIGS. 8 to 10 are plan views each showing the patterns of the first linear member 51 and the second linear member 52 in the main portion 22 of the catheter main body 2. To be more specific, FIGS. 8, 9 and 10 show the first region 221, the intermediate region 222 and the second region 223, respectively.

As shown in each of these drawings, the first linear member 51 denoted by black lines and the second linear member 52 denoted by white lines are braided on the outer surface of the base tube 4 to form a mesh structure. In the first region 221, the first and second linear members 51 and 52 are braided in high and low braiding densities, respectively, as shown in FIG. 8. In the intermediate region 222, the first and the second linear members 51 and 52 are braided in substantially the same braiding density, as shown in FIG. 9. Further, in the second region 223, the first and second linear members 51 and 52 are braided in low and high braiding densities, respectively, as shown FIG. 10. The other construction, the range of the numeral value, the function and the effect of this embodiment are substantially equal to those of the embodiment described previously and, thus, the description thereof is omitted.

Next, a method for manufacturing the catheter shown in FIGS. 8 to 10 will now be described. In the first step, the base tube 4 is prepared by the ordinary method. As described previously, it is possible for the base tube 4 to include the reinforcing layer 41 and the low friction layer 43. The first linear member 51 and the second linear member 52 are braided to form a mesh on the outer surface of the base tube 4.

Figure 11:
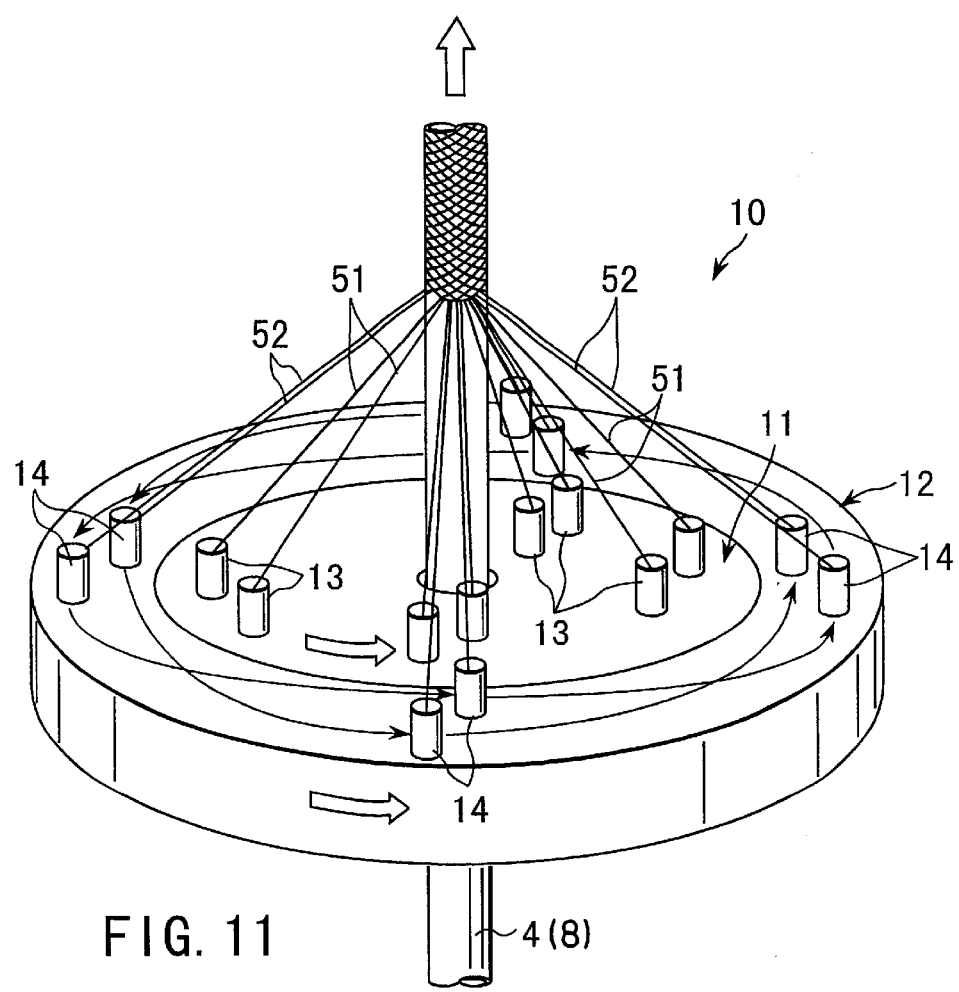
FIG. 11 is a perspective view showing a method of manufacturing a catheter according to another embodiment of the present invention.

FIG. 11 shows an apparatus 10 obtained by improving a known braider used for braiding the linear members. The linear member arranging apparatus 10 comprises an inside turntable 11 and an outside turntable 12, which are rotated concentrically. The base tube 4 is inserted substantially vertically into a central opening of the inside turntable 11.

Four pairs of carriers 13 (eight carriers in total), i.e., bobbin-like member for providing the linear member, acting a supply source of the first linear member 51 are mounted on the inside turntable 11. These four pairs are arranged 90° apart from each other. Likewise, four pairs of carriers 14 (eight carriers in total), acting a supply source of the second linear member 52 are mounted on the outside turntable 12. These four pairs are arranged 90° apart from each other. It is possible for these inside turntable 11 and outside turntable 12 to be rotated independent of each other.

On the inside turntable 11, the paired two carriers 13, which are positioned apart from each other in the radial direction of the inside turntable 11, are moved in accordance with rotation of the inside turntable 11 such that the carriers on the inside and outside positions are interchanged every time the inside turntable 11 is rotated by, for example, 90°. Likewise, on the outside turntable 12, the paired two carriers 14, which are positioned apart from each other in the radial direction of the outside turntable 12, are moved in accordance with rotation of the outside turntable 12 such that the carriers on the inside and outside positions are interchanged every time the outside turntable 12 is rotated by, for example, 90°.

The inside turntable 11 and the outside turntable 12 are rotated in the same direction while moving upward the base tube 4. As a result, eight first linear members 51 and eight second linear members 52 (16 linear members in total) are provided from the carriers 13 and 14, respectively, mounted on the inside turntable 11 and the outside turntable 12. In this case, the positions of the paired carriers 13 apart from each other in the radial direction of the inside turntable 11 are interchanged during rotation of the inside turntable 11, as already described. Also, the positions of the paired carriers 14 apart from each other in the radial direction of the inside turntable 12 are interchanged during rotation of the outside turntable 12. It follows that the first linear member 51 and the second linear member 52 are continuously wound around the outer surface of the base tube 5 to form the resin layer 5 in the form of a braided body.

Where the moving speed of the base tube 4 in its axial direction is set constant in the apparatus 10 described above, the winding densities of the first linear member 51 and the second linear member 52 around the base tube 4 depend on the rotating speeds (angular speeds) of the inside turntable 11 and the outside turntable 12, respectively. For example, where the rotating speed (angular speed) of the inside turntable 11 is set higher than that of the outside turntable 12, the first linear member 51 and the second linear member 52 are wound in high and low winding densities, respectively. Where the rotating speed (angular speed) of the inside turntable 11 is equal to that of the outside turntable 12, the first linear member 51 and the second linear member 52 are wound at substantially the same winding density. Further, where the rotating speed (angular speed) of the inside turntable 11 is set lower than that of the outside turntable 12, the first linear member 51 and the second linear member 52 are wound in low and high winding densities, respectively.

After the first and second linear members 51 and 52 are braided as described above, the braided bodies are melted by heating, followed by solidifying the molten material by cooling so as to form the resin layer 5 on the outer surface of the base tube 4. The heating method and conditions and the molten state of the linear members are as already described. Then, the outer surface of the resin layer 5 is covered with the outer layer 6, as desired. The covering method of the outer layer 6 is as already described. Further, the outer surface of the outer layer 6 is covered with a hydrophilic high molecular weight material, as desired, followed by mounting the hub 7 to the proximal end 21 of the catheter main body 2 so as to manufacture the catheter 1 of the present invention.

In the case where the first linear member 51 and the second linear member are disposed in a mesh configuration, it is possible to use another method in which the first linear member 51 and the second linear member 52 are braided around a mandrel in place of the base tube 4 and finally draw out the mandrel so as to manufacture the catheter as shown in FIG. 16. In this method, the catheter main body 2 that does not include the base tube 4 can be obtained. Such a method for manufacturing the catheter is described with referring to FIG. 11 and FIG. 19.

A mandrel 8 used in this method includes a metal wire made of, for example, copper, aluminum, gold, silver and stainless steel. In order to make it easy to draw out the mandrel finally, a release agent such as silicone oil, fluorinated oil, liquid paraffin or paraffin wax may be applied on the outer surface of the mandrel.

Next, the first linear member 51 and the second linear member 52 are braided around the mandrel 8. The linear member arranging apparatus 10 shown in FIG. 11 can be used for braiding these linear members as in the aforementioned method. The mandrel 8 is inserted substantially vertically into a central opening of the inside turntable 11. The inside turntable 11 and the outside turntable 12 are rotated in the same direction while moving upward the mandrel 8. As a result, eight first linear members 51 and eight second linear members 52 (16 linear members in total) are provided from the carriers 13 and 14, respectively, mounted on the inside turntable 11 and the outside turntable 12. In this case, the positions of the paired carriers 13 apart from each other in the radial direction of the inside turntable 11 are interchanged during rotation of the inside turntable 11. Also, the positions of the paired carriers 14 apart from each other in the radial direction of the inside turntable 12 are interchanged during rotation of the outside turntable 12. It follows that the first linear member 51 and the second linear member 52 are continuously wound around the outer surface of the mandrel 8 to form the resin layer 5 in the form of a braided body.

Where the moving speed of the mandrel 8 in its axial direction is set constant, the winding densities of the first linear member 51 and the second linear member 52 around the mandrel 8 depend on the rotating speeds (angular speeds) of the inside turntable 11 and the outside turntable 12, respectively. For example, where the rotating speed (angular speed) of the inside turntable 11 is set higher than that of the outside turntable 12, the first linear member 51 and the second linear member 52 are wound in high and low winding densities, respectively. Where the rotating speed (angular speed) of the inside turntable 11 is equal to that of the outside turntable 12, the first linear member 51 and the second linear member 52 are wound at substantially the same winding density. Further, where the rotating speed (angular speed) of the inside turntable 11 is set lower than that of the outside turntable 12, the first linear member 51 and the second linear member 52 are wound in low and high winding densities, respectively.

After the first and second linear members 51 and 52 are braided as described above, the braided bodies are melted by heating, followed by solidifying the molten material by cooling so as to form the flat resin layer 5 on the outer surface of the mandrel 8. The heating method and conditions and the molten state of the linear members are similar to those in the aforementioned method.

After the resin layer 5 is formed as described above, the outer surface of the resin layer 5 is covered with the outer layer 6, as desired. The covering methods of the outer layer 6 are similar to those in the aforementioned method.

Then, the mandrel 8 on which the resin layer 5 is formed is drawn out so as to obtain the shaped catheter main body 2. The drawing methods of the mandrel 8 are similar to those described with respect to the case where the first and second linear members 51 and 52 are arranged spirally.

In a manner as described above, a catheter main body 2 comprising a tubular resin layer 5 having a proximal end and a distal end and defining an inner lumen extending between the proximal end and the distal end is formed. A treatment to cover the outer surface of the outer layer 6 (or the resin layer 5 where the outer layer 6 is not formed) with a hydrophilic high molecular weight material may be performed, if desired. Then, the hub 7 is mounted to the proximal end 21 of the catheter main body 2 so as to manufacture the catheter 1 of the present invention. Incidentally, the treatment to cover with the hydrophilic high molecular weight material may be performed before the mandrel 8 is drawn out from the resin layer 5.

As described above, the winding densities of the first and second linear members 51 and 52 in the first region 221, the intermediate region 222 and the second region 223 can be controlled as desired by controlling appropriately the rotating speeds (angular speeds) of the inside turntable 11 and the outside turntable 12.

In the case of using the apparatus shown in FIG. 11, it is possible to arrange the first linear member 51 and the second linear member 52 at desired winding densities by simply controlling appropriately the rotating speeds of the carriers 13 and 14 relative to the base tube 4 or mandrel 8. It follows that the rigidity in each part of the catheter main body 2 can be controlled in a desired balance, making it possible to manufacture easily a catheter having characteristics adapted to the purpose of use and the case of the disease to be cured.

It is also possible to manufacture easily a catheter in which the winding densities of the first linear member 51 and the second linear member 52 are continuously changed in the axial direction of the catheter main body 2, if the relative rotating speeds of the carriers 13 and 14 are changed continuously.

In the embodiment described above, the braiding of the first linear member 51 and the braiding of the second linear member 52 are performed simultaneously. However, the braiding method is not particularly limited in the present invention. For example, the first linear member 51 may be braided first, followed by braiding the second linear member 52. By contraries, the second linear member 52 may be braided first, followed by braiding the first linear member 51. Further, the first linear member 51 and the second linear member 52 may be braided with a predetermined time difference.

The technical idea of the present invention can be applied to various catheters, not limited to an intracatheter described above. Such catheters include, for example, a guiding catheter, an angiography catheter, various balloon catheters for percutaneous transluminal coronary angioplasty (PTCA), for percutaneous transluminal angioplasty (PTA), for IABP, etc., an ultrasonic catheter, an atelectomy catheter, a catheter for an endoscope, an indwelling catheter, a catheter for administration of a medical solution, and an embolotherapy catheter (microcatheter) that is introduced into organs such the brain and the liver.

Next, a guiding catheter according to the present invention will be described. The guiding catheter is used for introducing a therapeutic catheter or a diagnostic catheter into a region in the vicinity of an aimed region with a body cavity.

Figure 12:
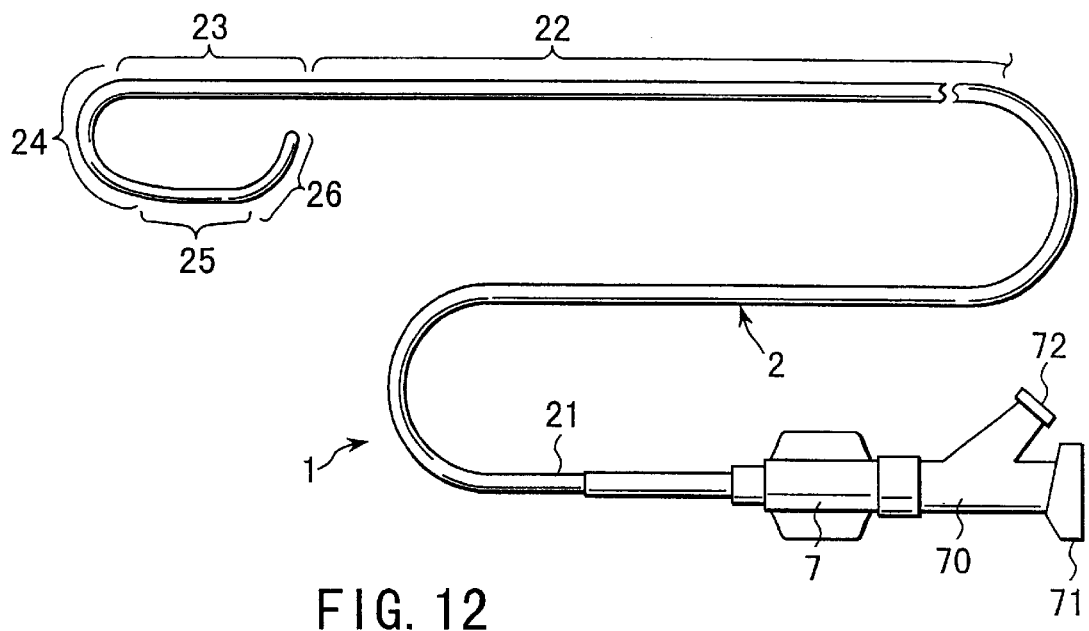
FIG. 12 is a plan view showing another example of the catheter of the present invention.
Figure 13:
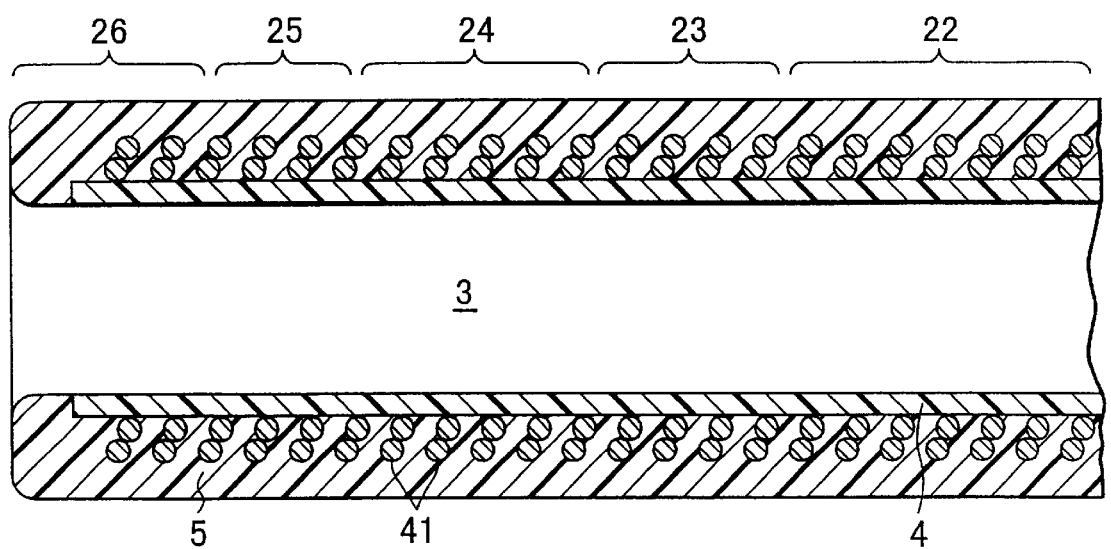
FIG. 13 is a cross sectional view of the catheter shown in FIG. 12.

FIG. 12 is a plan view showing an embodiment of a guiding catheter according to the present invention. FIG. 13 is a vertical cross sectional view of the guiding catheter shown in FIG. 12 in which the distal portion having a curved shape is depicted as is stretched linearly. The guiding catheter 1 shown in these drawings is for the left coronary arteries and has a curved distal end of a so-called Judkins type. In FIG. 12, the catheter main body 2 of the guiding catheter 1 is divided into a region 22, a region 23, a region 24, a region 25 and a region 26 as viewed from the proximal end 21. The guiding catheter 1 is designed such that the most greatly curved region 24 has a rigidity higher than those of the adjacent regions 23 and 25, i.e., the rigidity close to that of the region 22, in order to impart to the guiding catheter 1 back-up force for moderating the counteraction generated by insertion of a therapeutic catheter or a diagnostic catheter.

The technical idea of the present invention can also be applied to a guiding catheter having another curved shape such as an Ampratz type or to a guiding catheter used for other diseased portions such as right coronary arteries or the head portion.

As shown in FIG. 12, the catheter 1 comprises the catheter main body 2, the hub 7 mounted to the proximal end 21 of the catheter main body 2, and a Y-connector 70. The inner lumen 3 is formed inside the catheter main body 2 in a manner to extend from the proximal end 21 to the distal end. The guide wire and other medical instrument such as a PTCA dilatation catheter are introduced through a port 72 of the Y-connector 70 so as to be inserted into the inner lumen 3 of the catheter main body 2 through the inner lumens of the Y-connector 70 and the hub 7. A tubular branched portion 71 is formed in the Y-connector 70. The branched portion 71 is used for injecting an x-ray contrast medium into a desired region within a blood vessel. The X-ray contrast medium injected through the branched portion 71 is discharged from an opening at the distal end through the inner space of the Y-connector 70 and the inner lumen 3 of the catheter main body 2. The outer diameter of the catheter main body 2, which is smaller than the diameter of the ostium' of the coronary arteries, is not larger than 10 Fr (3.33 mm). As shown in FIG. 13, the catheter main body 2 consists of the base tube 4, the reinforcing layer 41 formed on the outer surface of the base tube 4 and the resin layer 5 covering the outer surface of the reinforcing layer 41.

As described previously, the catheter main body 2 is divided into five regions of the region 22, the region 23, the region 24, the region 25 and the region 26 as viewed from the proximal end 21. The first linear member having a relatively high rigidity and the second linear member having a relatively low rigidity are used for forming the resin layer 5 in each of these regions 22 to 26. Specifically, these first and second linear members are wound spirally as shown in FIGS. 4 and 5 or to form a mesh as shown in FIGS. 8 to 10 around the base tube 4, followed by melting and, then, solidifying the molten material so as to form the resin layer 5.

To be more specific, each region of the guiding catheter in this embodiment is constructed as follows. Specifically, the resin layer 5 in the region 22 is formed by arranging the first linear member alone around the base tube 4. The resin layer 5 in the region 23 is formed by arranging the first linear member in a low arranging density and the second linear member in a high arranging density around the base tube 4. The resin layer 5 in the region 24 is formed by arranging the first linear member in a high arranging density and the second linear member in a low arranging density around the base tube 4. The resin layer 5 in the region 25 is formed by arranging the first linear member in a low arranging density and the second linear member in a high arranging density around the base tube 4. Further, the resin layer 5 in the region 26 is formed by arranging the second linear member alone around the base tube 4.

Because of the particular construction described above, the region 22 has a sufficient flexural rigidity, and the region 26 is highly flexible, leading to a high safety. On the other hand, in the regions 23, 24 and 25 interposed between the region 22 and the region 26, the flexural rigidity is lower than that in the region 22 and higher than that in the region 26. As a result, a rapid change in the flexural rigidity is prevented from the region 22 over the region 26. Also, the region 24 has a rigidity higher than that of the adjacent regions 23 and 24. Therefore, the region 24 imparts to the catheter main body 2 a back-up force for moderating the counteraction generated by the insertion of, for example, a therapeutic catheter so as to make it possible to introduce smoothly the therapeutic catheter to a desired region.

It is desirable to change gradually the arranging densities of the first and second linear members at the boundaries between adjacent regions in the regions 22 to 26 so as to make the change in the flexural rigidity more moderate.

In this embodiment, it is desirable for the first linear member to be made of a resin material having a flexural modulus of elasticity of 14,000 to 15,500 kg/cm² and a Shore D hardness of 65 to 74. Also, it is desirable for the second linear member to be made of a resin material having a flexural modulus of elasticity of 150 to 520 kg/cm² and a Shore D hardness of 29 to 38.

Concerning the densities of the first linear member and the second linear member in the regions 23 and 25, it is desirable for the areal ratio or weight ratio of the first linear member to the second linear member to fall within a range of between 1:9 and 5:5, preferably between 2:8 and 3:7.

Concerning the densities of the first linear member and the second linear member in the region 24, it is desirable for the areal ratio or weight ratio of the first linear member to the second linear member to fall within a range of between 9:1 and 5:5, preferably between 8:2 and 7:3.

The first and second linear members wound or braided around the base tube 4 and the reinforcing layer 41 are at least partially melted by heating and, then, solidified to form the resin layer 5. The heating method and the heating conditions and the 56 molten state of the linear members are as described previously. Therefore, it is desirable for the first and second linear members to be compatible with each other. Suitable combinations of the first and second linear members include, for example, a combination or polyurethane and polyamide, a combination of polyamide and polyamide elastomer, a combination of polyethylene or polypropylene and polyolefin elastomer, a combination of polyethylene terephthalate and polyester elastomer, a combination of polyurethane and polyester elastomer, and a combination of a high plasticizing polyvinyl chloride and a low plasticizing polyvinyl chloride. In particular, a combination of polyamide having a high rigidity and polyamide elastomer having a low rigidity and a combination of polyurethane having a high rigidity and polyester elastomer having a low rigidity are suitable.

It is desirable for the resin layer 5 to have a thickness of 10 to 150 μm. The thickness of the resin layer 5, i.e., outer diameter of the catheter main body 2, need not be constant over the entire length of the catheter 1. For example, if the outer diameter of the catheter 1 in a region on the side of the proximal end is made larger than that in a region on the side of the distal end portion, it is possible to improve the flexural rigidity.

The lengths of the regions 22 to 26, which depend on the shape, kind, etc., of the catheter, are not particularly limited. When it comes to a guiding catheter for the left coronary arteries of Judkins type as shown in the drawing, it is desirable for the lengths of these regions to be set as follows. Specifically, it is desirable for the length of the region 22 to be 500 to 1000 mm, for the length of the region 23 to be 80 to 150 mm, for the length of the region 24 to be 20 to 80 mm, for the length of the region 25 to be 5 to 20 mm, and for the length of the region 26 to be 2 to 15 mm.

In this embodiment, the rigidity of the region 24 is made higher than that of each of the regions 23 and 25 in order to improve the back-up force. However, it is also possible to change gradually the densities of the first and second linear members over the regions 23 to 25 such that the rigidity is gradually changed from that similar to the region 22 on the side of the proximal end to that similar to the region 26 on the side of the distal end. The manner of the change in the rigidity may be continuous or stepwise.

The other members of the catheter of the present invention will now be described.

The base tube 4, which defines the inner lumen 3, is made of a low friction material. Since the inner surface of the base tube 4 has a low friction, it is possible to decrease the sliding resistance of the guide wire, dilatation catheter or the like inserted into the inner lumen 3. It follows that it is possible to perform easily and smoothly the operation for inserting the catheter 1 into a blood vessel along the preceding guide wire and the operation for drawing out the guide wire from the catheter 1.

It is possible to use any material for forming the base tube 4 as far as the friction of the inner surface can be lowered. For example, it is possible to use a fluoroplastics, nylon 66, polyether ether ketone, polyethylene or polyamide for forming the base tube 4. In particular, the fluoroplastics is more preferable.

The fluoroplastics includes, for example, polytetrafluoroethylene, polyvinylidene fluoride, ethylenetetrafluoroethylene copolymer, and perfluoroalkoxy resin. In particular, polytetrafluoroethylene is more preferable.

The thickness of the base tube 4 is not particularly limited in the present invention, though it is desirable for the thickness of the base tube 4 to be not larger than 50 μm, particularly not larger than 40 μm. If the thickness of the base tube 4 is unduly large, it is difficult to diminish the diameter of the catheter main body 2.

As shown in FIG. 13, it is desirable for the base tube 4 not to be arranged in a region ranging between an intermediate portion of the region 26 and the distal end. In this construction, the flexibility in the distal end portion of the catheter main body 2 is improved so as to prevent the inner wall of a blood vessel from being damaged, leading to an improved safety.

The reinforcing layer 41 is formed on the outer surface of the base tube 4. It is desirable for the reinforcing layer 41 to be formed of, for example, a braided body of a metal wire such as a steel wire or a stainless steel wire in view of the pushability, the torque transmitting capability, the kink resistance and the pressure resistance. Other examples of the reinforcing layer 41 include, for example, a coil of a hard material such as a metal and a slit tube made of a hard material such as a metal.

The metal wire constituting the reinforcing layer 41 is not limited to a wire having a circular cross section as shown in the drawing. It is also possible to use a metal ribbon having a flat cross section. It is desirable for the metal wire having a circular cross section to have a diameter of 10 to 70 μm, preferably 30 to 50 μm. It is desirable for the metal ribbon to have a width of 100 to 200 μm and a thickness of 10 to 50 μm.

The reinforcing layer 41 extends from a point a predetermined distance away from the distal end of the base tube 4 to cover a region on the side of the proximal end of the region 26, and the regions 25, 24, 23 and 22. Since the reinforcing layer 41 is not arranged to cover a region on the side of the distal end of the region 26, the flexibility is improved in the distal end portion of the catheter main body 2 so as to prevent the inner wall of a blood vessel from being damaged, leading to an improved safety.

It is possible to add an X-ray contrast medium containing, for example, a metal powder made of platinum, gold, silver, tungsten or an alloy thereof, barium sulfate, bismuth oxide or a coupling agent thereof to the first linear member, the second linear member or the base tube 4. In this case, the position of the catheter main body 2 can be visually recognized under fluororoentgenography during use of the catheter.

A microcatheter (embolotherapy catheter) of the present invention will now be described. The microcatheter is used for administering various therapeutic medicines, thrombolic materials, contrast media, etc., into desired regions of the brain and abdomen organs.

Figure 14:
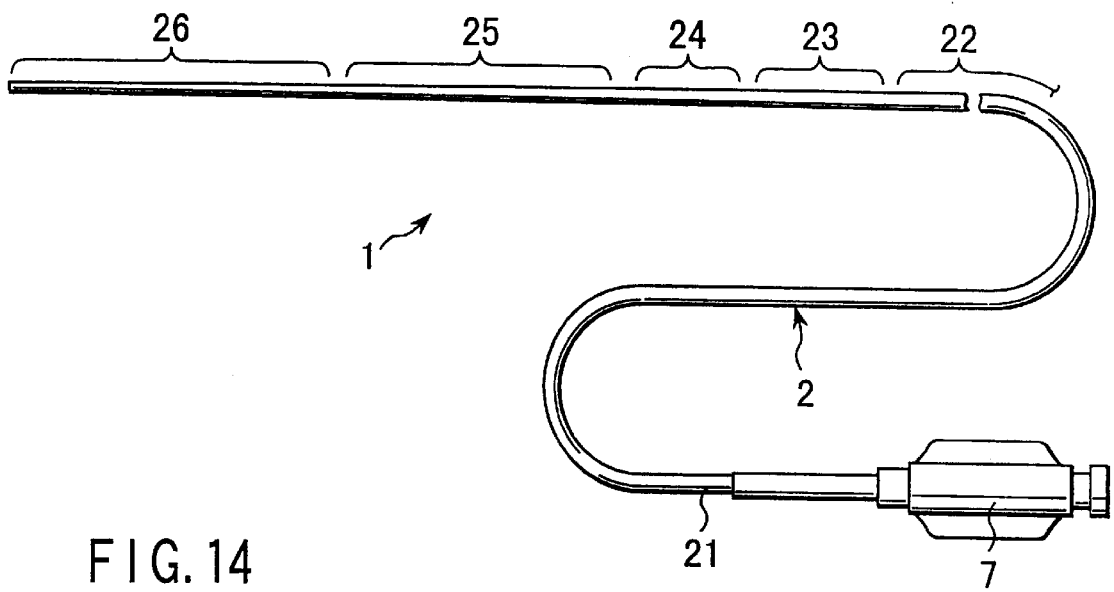
FIG. 14 is a plan view showing another example of the catheter of the present invention.
Figure 15:
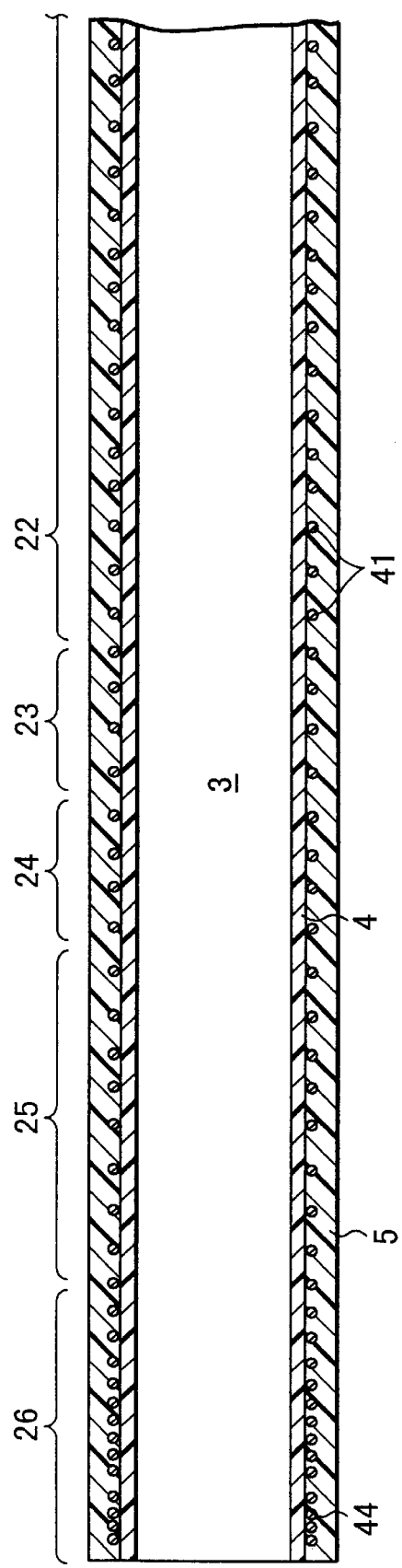
FIG. 15 is a cross sectional view of the catheter shown in FIG. 14.

FIG. 14 is a plan view showing a microcatheter according to an embodiment of the present invention, and FIG. 15 is a vertical cross sectional view of the catheter shown in FIG. 14.

As shown in FIG. 14, the catheter 1 comprises the catheter main body 2, and the hub 7 mounted to the proximal end 21 of the catheter main body 2. The inner lumen 3 is formed within the catheter main body 2 in a manner extending from the proximal end 21 to the distal end. When the catheter 1 is inserted into a blood vessel, a guide wire is inserted into the inner lumen 3. The inner lumen 3 is also used as a fluid passageway of an X-ray contrast medium, a medical solution, etc. As shown in FIG. 15, the catheter main body 2 comprises the base tube 4, the reinforcing layer 41 formed on the outer surface of the base tube 4, and the resin layer 5 formed on the outer surface of the reinforcing layer 41.

In FIG. 14, the catheter main body 2 is divided into the region 22, the region 23, the region 24, the region 25 and the region 26 in the order mentioned as viewed from the proximal end 21. The resin layer 5 in each of these regions is formed by arranging each of a first linear member having a relatively high rigidity and a second linear member having a relatively low rigidity in a spiral form as shown in FIGS. 4 and 5 or in a mesh form as shown in FIGS. 8 to 10, followed by melting and, then, solidifying these first and second linear members.

To be more specific, each region of the microcatheter in this embodiment is constructed as follows. Specifically, the resin layer 5 in the region 22 is formed by arranging the first linear member alone around the base tube 4. The resin layer 5 in the region 23 is formed by arranging the first linear member in a high arranging density and the second linear member in a low arranging density around the base tube 4. The resin layer 5 in the region 24 is formed by arranging the first and second linear members in the intermediate arranging densities relative to those in the regions 23 and 25 around the base tube 4. The resin layer 5 in the region 25 is formed by arranging the first linear member in a low arranging density and the second linear member in a high arranging density around the base tube 4. Further, the resin layer 5 in the region 26 is formed by arranging the second linear member alone around the base tube 4.

Because of the particular construction described above, the region 22 has a sufficient flexural rigidity, and the region 26 is highly flexible, leading to a high safety. Also, the flexural rigidity of the catheter main body 2 is gradually diminished from the proximal end portion toward the distal end portion in the order of the regions 22, 23, 24, 25 and 26, making it possible to obtain excellent following capability and kink resistance.

Within each region, the arranging density of each of the first linear member and the second linear member may be set constant, though it is desirable to change gradually in the longitudinal direction of the catheter the arranging density of each of the first linear member and the second linear member in the boundary region between adjacent regions within the regions 22 to 26 so as to make the change in the flexural rigidity more moderate. Further, it is desirable to change continuously or stepwise the ratio of the first linear member to the second linear member within the regions 23, 24 and 25 so as to decrease more continuously the flexural rigidity of the catheter main body 2 toward the distal end of the catheter.

In this embodiment, it is desirable for the first linear member to be made of a resin material having a flexural modulus of elasticity of 14,000 to 15,500 $kg/cm^2$ and a Shore D hardness of 65 to 74. Also, it is desirable for the second linear member to be made of a resin material having a flexural modulus of elasticity of 150 to 520 $kg/cm^2$ and a Shore D hardness of 29 to 38.

Concerning the arranging density of each of the first linear member and the second linear member in the region 23, it is desirable for the areal ratio or weight ratio of the first linear member to the second linear member to fall within a range of between 40:60 and 99:1, preferably between 50:50 and 95:5.

Concerning the arranging density of each of the first linear member and the second linear member in the region 24, it is desirable for the areal ratio or weight ratio of the first linear member to the second linear member to fall within a range of between 20:80 and 60:40, preferably between 30:70 and 50:50.

Further, concerning the arranging density of each of the first linear member and the second linear member in the region 25, it is desirable for the areal ratio or weight ratio of the first linear member to the second linear member to fall within a range of between 1:99 and 40:60, preferably between 5:95 and 30:70.

The first and second linear members arranged on the base tube 4 and the reinforcing layer 41 are at least partially melted by heating and, then, solidified to form the resin layer 5. The heating method, the heating conditions and the molten state of the linear members are as already described. Therefore, it is desirable to select the resin materials of the first and second linear members compatible with each other. Suitable combinations of the first and second linear members include, for example, a combination of polyamide having a high rigidity and polyamide elastomer having a low rigidity, and a combination of polyurethane having a high rigidity and polyester elastomer having a low rigidity.

It is desirable for the resin layer 5 to have a thickness of 50 to 200 μm. The thickness of the resin layer 5, i.e., the outer diameter of the catheter main body 2, may not be constant over the entire length of the catheter 1. For example, if the outer diameter of the catheter 1 in a region on the side of the proximal end is made larger than that in a region on the side of the distal end, the flexural rigidity can be increased.

The lengths of the regions 22 to 26, which are set appropriately depending on the shape, kind, etc., of the catheter, are not particularly limited in the present invention. When it comes to the microcatheter shown in the drawings, it is desirable for the region 22 to be 750 to 1300 mm long, for the region 23 to be 5 to 100 mm long, for the region 24 to be 5 to 100 mm long, for the region 25 to be 100 to 300 mm long, and for the region 26 to be 5 to 100 mm long.

The other members of the microcatheter of the present invention will now be described.

The base tube 4, which defines the inner lumen 3, is made of a low friction material. Since the inner surface of the base tube 4 has a low friction, it is possible to decrease the sliding resistance of the guide wire, the dilatation catheter, etc., inserted into the inner lumen 3. It follows that it is possible to perform easily and smoothly the operation for inserting the catheter 1 into a blood vessel along the preceding guide wire and the operation for drawing out the guide wire from the catheter 1.

The base tube 4 can be formed of any material as far as it is possible to decrease the friction on the inner surface of the base tube 4. For example, it is possible to use fluoroplastics, nylon 66, polyether ether ketone, polyethylene or polyimide. Particularly, fluoroplastics is more preferable.

The fluoroplastics used in the present invention includes, for example, polytetrafluoroethylene, polyvinylidene fluoride, and perfluoroalkoxy resin. Particularly, polytetrafluoroethylene is more preferable.

The thickness of the base tube 4 is not particularly limited, though it is desirable for the thickness of the base tube 4 to be not larger than 50 µm, preferably not larger than 40 µm. If the base tube 4 is unduly thick, it is difficult to diminish the diameter of the catheter main body 2.

In FIG. 15, the base tube 4 is arranged to extend over the entire length of the catheter main body 2. However, it is not absolutely necessary for the base tube 4 to extend over the entire length of the catheter main body 2. For example, it is possible for the base tube 4 not to be present in a region ranging between an intermediate portion of the region 26 and the distal end.

The reinforcing layer 41 for reinforcing the catheter main body 2 is formed on the outer surface of the base tube 4. In this embodiment, the reinforcing layer 41 is formed of a coil. Alternatively, the reinforcing layer 41 may be formed of a braided body of a metal wire, a slit metal tube or the like. It is also possible to use a braided body and a coil in combination. For example, a braided body is formed on the side of the proximal end and the coil is formed on the side of the distal end of the base tube 4. Further, it is possible to laminate the braided body and the coil on the outer surface of the base tube 4.

A metal or a non-metallic material can be used for forming the coil. For example, it is possible to wind spirally a metal material to form the coil, to wind spirally a non-metallic material to form the coil, o r to wind spirally a laminate structure consisting of a metal layer and a non-metal layer to form the coil.

The metal material includes, for example, stainless steel, nickel-titanium alloy, platinum, iridium and tungsten. These metal materials can be used singly or in combination.

The non-metal material includes, for example, carbon, polyamide, polyethylene terephthalate, and polybutylene terephthalate. These materials can be used singly or in combination.

The winding pitch of the coil, which is not particularly limited, should desirably be 2 mm or less, preferably 0.02 to 0.5 mm. Where the winding pitch of the coil falls within the range noted above, an appropriate rigidity can be imparted to the catheter main body 2. It is not absolutely necessary for the winding pitch of the coil to be uniform over the entire length of the catheter. In other words, the winding pitch can be changed appropriately depending on the region of the catheter main body.

The metal wire constituting the reinforcing layer 41 is not limited to a wire having a circular cross section. It is possible to use, for example, a metal ribbon having a flat cross section for forming the reinforcing layer 41. It is desirable for the metal wire having a circular cross section to have a diameter of 0.03 to 0.06 mm, preferably 0.04 to 0.05 mm. On the other hand, the metal ribbon should desirably have a width of 0.1 to 1.0 mm and a thickness of 0.01 to 0.05 mm.

The reinforcing layer 41 consisting of such a coil or a braided body produces a sufficient reinforcing effect even if the reinforcing layer 41 is relatively thin. Therefore, the catheter main body 2 having the reinforcing layer 41 is advantageous in diminishing the diameter.

In this embodiment, a marker 44 opaque to an X-ray is arranged in that portion of the region 26 on the side of the distal end. The marker 44 opaque to the X-ray is arranged in order to visually confirm the position of the catheter main body 2 under the fluororoentgenography when the catheter main body 2 is inserted into a blood vessel. The marker 44 may have any form such as a coil or a ring. It is possible to arrange the marker 44 opaque to the X-ray in an optional position within the reinforcing layer 41. Also, it is possible to arrange the marker 44 in a single or a plurality of positions. In this embodiment, the X-ray opaque marker 44 is formed in a single position closer to the distal end than the reinforcing layer 41 in the form of a coil having a small winding pitch.

The material of the X-ray opaque marker 44 includes, for example, gold, platinum, iridium, tungsten and an alloy thereof. These materials can be used singly or in combination.

Incidentally, if a coil of, for example, tungsten is used as the reinforcing layer 4 and the winding pitch of the coil in a region on the side of the distal end is set at, for example, 0.05 mm or less, the particular portion of the reinforcing layer 41 can be used as the marker 44 opaque to the X-ray. In this case, the reinforcing layer 41 and the X-ray opaque marker 44 can be formed of the same wire or ribbon.

Also, it is possible to add an X-ray contrast medium containing a metal powder of, for example, platinum, gold, silver, tungsten or an alloy thereof, barium sulfate, bismuth oxide or a coupling compound thereof to the first linear member, the second linear member or the base tube 4.

In the catheter 1 in this embodiment, it is desirable to cover the surface of the catheter main body 2, i.e., the surface on the side of at least the distal end of the resin layer 5, with a hydrophilic high molecular weight material (not shown). In this case, lubricity is obtained when the outer surface of the catheter main body 2 is brought into contact with a liquid material such as blood or a physiological saline so as to decrease the frictional resistance of the catheter main body 2 and, thus, to further improve the sliding properties. As a result, the operability, particularly, the pushability, following capability, kink resistance and safety, can be further improved in the step of the catheter insertion.

On the other hand, the proximal end portion of the catheter main body 2 is manually operated in the step of inserting the catheter 1 into a blood vessel. If the catheter main body 2 slides within the operator's hand in inserting the catheter 1 into a blood vessel, the operability of the catheter 1 is lowered. Therefore, it is desirable for, for example, 150 to 500 mm of the proximal end portion of the catheter main body 2 not to be covered with a hydrophilic high molecular weight material.

The hydrophilic high molecular weight material includes, for example, a natural or synthetic high molecular weight material and derivatives thereof. Particularly, it is desirable to use a cellulose-based high molecular weight material such as hydroxypropyl cellulose, a polyethylene oxide-based high molecular weight material such as polyethylene glycol, a maleic anhydride-based high molecular weight material such as maleic anhydride copolymer like methyl vinyl ethermaleic anhydride copolymer, an acrylamide-based high molecular weight material such as polyacrylamide, a water-soluble nylon such as AQ-nylon P-70 manufactured by Toray Inc. because a low friction coefficient can be obtained stably in these materials. A maleic anhydride-based high molecular weight material is used in the present invention as the most desirable hydrophilic high molecular weight material. Further, the derivative prepared by making the water-soluble high molecular weight material insoluble can also be used as far as the molecular chain has a degree of freedom and the derivative is capable of absorbing water.

In order to have the outer surface of the catheter main body 2 covered with a hydrophilic high molecular weight material, it is desirable for the high molecular weight material to form a covalent bond with the reactive functional group present in or introduced into the resin layer 5 or the surface of the resin layer 5. In this case, it is possible to obtain a sustainable lubricating surface.

Any type of the reactive functional group can be used as far as the functional group performs reaction with the hydrophilic high molecular weight material to form a chemical bond or crosslinkage. The reactive functional group employed includes, for example, diazonium group, azide group, isocyanate group, acid chloride group, acid anhydride group, imino carbonate group, amino group, carboxyl group, epoxy group, hydroxyl group, and aldehyde group. Particularly, it is desirable to employ isocyanate group, amino group, aldehyde group and epoxy group as the reactive functional group.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method for manufacturing a catheter comprising a tubular member having a proximal end and a distal end, and defining an inner lumen extending between the proximal end and the distal end, the method comprising steps of:

preparing a first linear member made of a first resin material and a second linear member made of a second resin material;

disposing said first linear member in the form of a dense spiral or mesh on a first region of said tubular member and in the form of a sparse spiral or mesh on a second region of said tubular member, thereby forming a first resin layer; and disposing said second linear member in the form of a sparse spiral or mesh on the first region of said tubular member and in the form of a dense spiral or mesh on the second region of said tubular member, thereby forming a second resin layer.

2. The method according to claim 1, further comprising steps of:

disposing said first linear member in an intermediate region between said first region and said second region in a disposing density intermediate between the disposing densities in the first region and second region; and disposing said second linear member in an intermediate region between said first region and said second region in a disposing density intermediate between the disposing densities in the first region and second region.

3. The method according to claim 2, wherein said first region, said intermediate region and said second region are arranged in the order mention as viewed from the proximal end of said tubular member.

4. The method according to claim 1, wherein a supply source of the first linear member and a supply source of the second linear member are rotated around said tubular member and the relative rotating speeds of these supply sources are adjusted so as to adjust the disposing densities of the first and second linear members on said tubular member.

5. The method according to claim 1, wherein said first linear member has a flexural rigidity higher-than that of said second linear member.

6. The method according to claim 1, further comprising steps of:

melting at least partially the first and second linear members disposed on the tubular member so as to mix or fuse; and solidifying these first and second linear members.

7. The method according to claim 1, further comprising steps of:

covering the first and second linear members disposed on the tubular member with a heat shrinkable tube;

heating the first and second linear members covered with the heat shrinkable tube, thereby melting at least partially the first and second linear members so as to mix or fuse; and solidifying these first and second linear members.

8. The method according to claim 1, further comprising a step of disposing the first linear member alone in a region on the side of the proximal end relative to said first region.

9. The method according to claim 1, further comprising a step of disposing the second linear member alone in a region on the side of the distal end relative to said second region.

10. A catheter comprising a tubular member having a proximal end and a distal end, and defining an inner lumen between the proximal end and the distal end, the catheter comprising:

a first resin layer disposed on a first region of said tubular member and constituted by a first resin material formed into a dense spiral or mesh and a second resin material formed into a sparse spiral or mesh; and a second resin layer disposed on a second region of said tubular member and constituted by the second resin material formed into a dense spiral or mesh and the first resin material formed into a sparse spiral or mesh.

11. The catheter according to claim 10, further comprising a resin layer disposed in an intermediate region between said first region and said second region of said tubular member and consisting of said first resin material disposed in the form of a spiral or mesh in a disposing density intermediate between the disposing densities in the first and second regions and said second resin material disposed in the form of a spiral or mesh in a disposing density intermediate between the disposing densities in the first and second regions.

12. The catheter according to claim 11, wherein said first region, said intermediate region and said second region are positioned in the order mentioned as viewed from the proximal end of the tubular member.

13. The catheter according to claim 11, further comprising a resin layer formed of said first resin material alone and disposed in a region on the side of the proximal end relative to the first region of the tubular member.

14. The catheter according to claim 12, further comprising a resin layer formed of said second resin material alone and disposed in a region on the side of the distal end relative to the second region of said tubular member.

15. The catheter according to claim 10, wherein:

second resin layers consisting of the second resin material in the form of a dense spiral or mesh and the first resin material in the form of a sparse spiral or mesh are disposed in two second regions on the sides of the proximal end and the distal end, respectively, of the first region of said tubular member; and the second region on the side of the proximal end, the first region, and the second region on the side of the distal end are positioned in the order mentioned as viewed from the proximal end of said tubular member.

16. The catheter according to claim 15, further comprising a resin layer formed of said first resin material alone and disposed in a region on the side of the proximal end relative to the second region on the side of the proximal end.

17. The catheter according to claim 15, further comprising a resin layer formed of said second resin material alone and disposed in a region on the side of the distal end relative to the second region on the side of the distal end.

18. The catheter according to claim 10, wherein the first resin material has a flexural rigidity higher than that of the second resin material.

19. The catheter according to claim 10, wherein each of said first and second resin layers is formed by melting at least partially the first resin material and the second resin material to mix or fuse these first and second resin materials, followed by solidifying the mixed or fused resin materials.

20. The catheter according to claim 10, wherein at least one of said first and second resin materials is partially melted to retain the skeleton thereof.

21. The catheter according to claim 10, wherein said first and second resin layers are formed in regions excluding the distal end portion of said tubular member.

22. The catheter according to claim 10, further comprising a reinforcing layer made of a metal and covering said tubular member.

23. The catheter according to claim 22, wherein said reinforcing layer consists of a braided body of a metal wire or a metal ribbon.

24. The catheter according to claim 10, further comprising a low friction layer formed on the inner surface of said tubular member.

25. The catheter according to claim 10, further comprising an outer layer formed on said first and second resin layers.

26. A method for manufacturing a catheter comprising steps of:

preparing a first linear member made of a first resin material, a second linear member made of a second resin material, and a mandrel;

disposing said first linear member in the form of a dense spiral or mesh on a first region of said mandrel and in the form of a sparse spiral or mesh on a second region of said mandrel;

disposing said second linear member in the form of a sparse spiral or mesh on the first region of said mandrel and in the form of a dense spiral or mesh on the second region of said mandrel;

melting at least partially said first and second linear members disposed on said mandrel so as to mix or fuse;

solidifying these first and second linear members; and drawing out said mandrel, thereby forming a catheter comprising a resin layer having a proximal end and a distal end, and defining an inner lumen extending between the proximal end and the distal end.

27. A catheter comprising a resin layer having a proximal end and a distal end, and defining an inner lumen extending between the proximal end and the distal end, wherein a first region of said resin layer consists of a first resin layer constituted by a first resin material formed into a dense spiral or mesh and a second resin material formed into a sparse spiral or mesh, and a second region of said resin layer consists of a second resin layer constituted by the second resin material formed into a dense spiral or mesh and the first resin material formed into a sparse spiral or mesh.

* * * * *